(12) United States Patent
Han et al.

(10) Patent No.: US 12,247,240 B2
(45) Date of Patent: Mar. 11, 2025

(54) RECOMBINANT MICROORGANISM HAVING INCREASED ABILITY TO PRODUCE ISOPROPANOL AND METHOD OF PRODUCING ISOPROPANOL USING SAME

(71) Applicant: Korea University Research and Business Foundation, Seoul (KR)

(72) Inventors: Sung Ok Han, Seoul (KR); Young Jin Ko, Chuncheon-si (KR); Joy Cha, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 18/062,834

(22) Filed: Dec. 7, 2022

(65) Prior Publication Data
US 2023/0272436 A1 Aug. 31, 2023

(30) Foreign Application Priority Data
Dec. 22, 2021 (KR) .................. 10-2021-0185265

(51) Int. Cl.
*C12P 7/04* (2006.01)
*C12N 15/77* (2006.01)

(52) U.S. Cl.
CPC .............. *C12P 7/04* (2013.01); *C12N 15/77* (2013.01)

(58) Field of Classification Search
CPC ................................. C12P 7/04; C12N 15/77
See application file for complete search history.

(56) References Cited

U.S. PATENT DOCUMENTS

| | | | | |
|---|---|---|---|---|
| 2011/0165642 A1* | 7/2011 | Yukawa et al. | ........... | C12P 7/04 435/157 |
| 2016/0138058 A1* | 5/2016 | Wittmann | ................. | C12P 7/52 435/141 |

FOREIGN PATENT DOCUMENTS

| KR | 10-2010-0087695 A | 8/2010 |
|---|---|---|
| KR | 10-2011-0021797 A | 3/2011 |
| KR | 10-1284015 B1 | 7/2013 |
| KR | 10-2013-0129654 A | 11/2013 |

OTHER PUBLICATIONS

Hu et al. Microbial production of acetoacetate by recombinant *Escherichia coli*. Bioresource Technology. (2010) 8477-8480. (Year: 2010).*
Bakkes PJ, Ramp P, Bida A, Dohmen-Olma D, Bott M, Freudl R. Improved pEKEx2-derived expression vectors for tightly controlled production of recombinant proteins in Corynebacterium glutamicum. Plasmid. Nov. 2020;112:102540. doi: 10.1016/j.plasmid.2020. 102540. Epub Sep. 28, 2020. PMID: 32991924. (Year: 2020).*
Korean Office Action issued on Jan. 20, 2024, in counterpart Korean Patent Application No. 10-2021-0185265 (4 pages in English, 4 pages in Korean).
Korean Office Action issued on Sep. 26, 2024, in counterpart Korean Patent Application No. 10-2021-0185265 (5 pages in English, 5 pages in Korean).

* cited by examiner

*Primary Examiner* — Louise W Humphrey
*Assistant Examiner* — John Paul Selwanes
(74) *Attorney, Agent, or Firm* — NSIP Law

(57) ABSTRACT

Disclosed are an expression cassette for isopropanol production, a recombinant vector for isopropanol production expression cassette, a including the recombinant microorganism for isopropanol production into which the vector is introduced, and a method of producing isopropanol using the recombinant microorganism. The recombinant microorganism in which a succinic acid bypass metabolic pathway is introduced to an isopropanol production pathway has very high ability to produce isopropanol. The recombinant microorganism is capable of producing isopropanol in an amount corresponding to about 100 times the maximum amount of isopropanol that is produced using known *Corynebacterium glutamicum*, and thus can effectively produce isopropanol and can be useful in various industrial fields where isopropanol is utilized. The use of the recombinant microorganism makes possible eco-friendly production of high-value-added isopropanol materials for manufacturing biomass-derived chemical products using glucose in lieu of petroleum.

7 Claims, 19 Drawing Sheets
Specification includes a Sequence Listing.

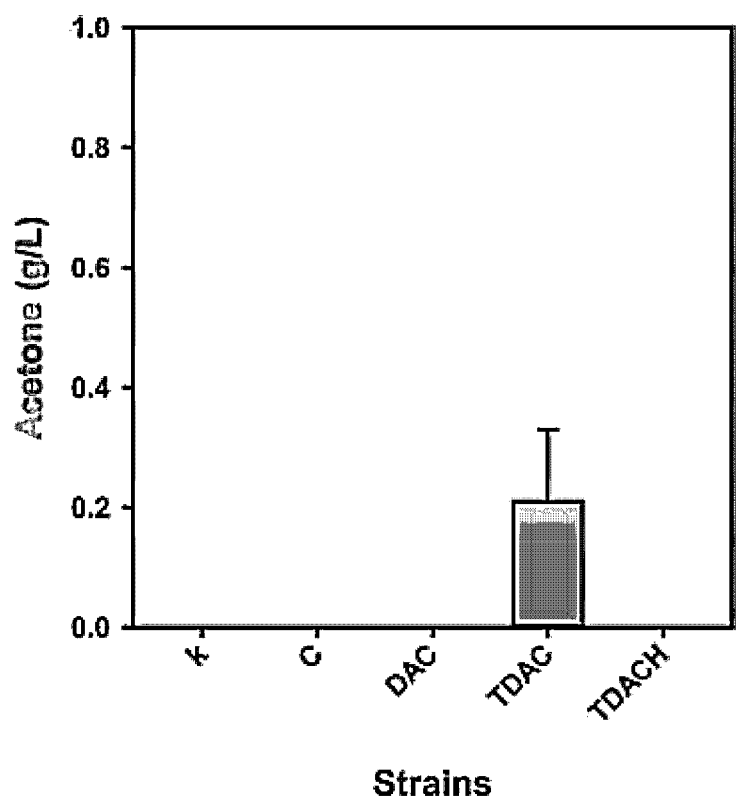

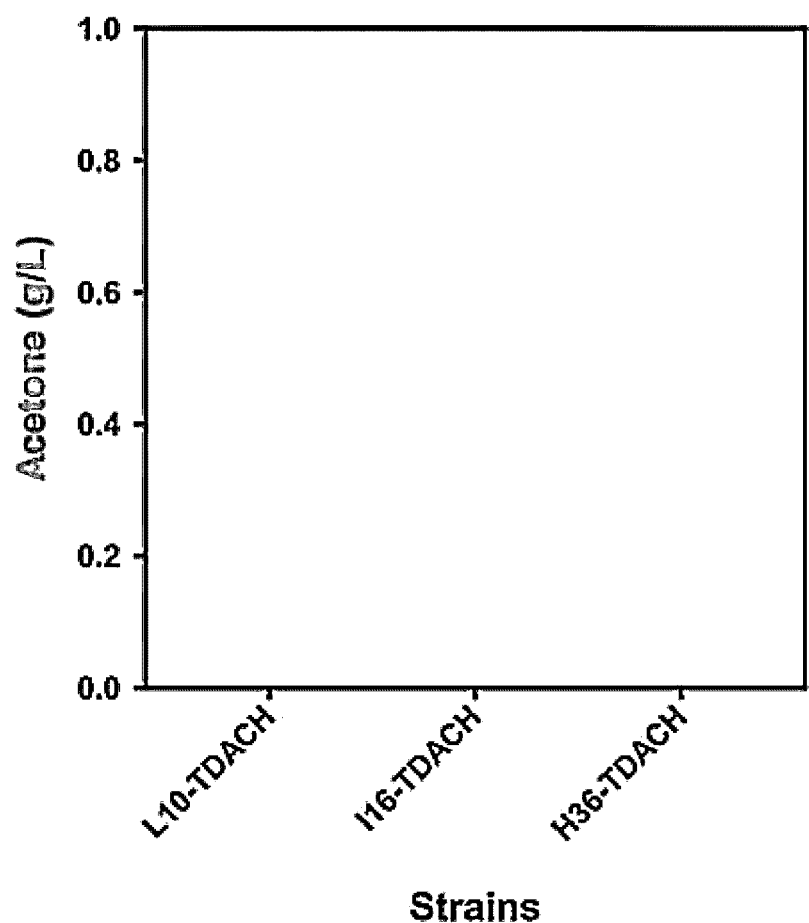

SEQUENCE LISTING

```
Sequence total quantity: 38
SEQ ID NO: 1            moltype = DNA  length = 1179
FEATURE                 Location/Qualifiers
misc_feature            1..1179
                        note = polynucleotide sequence of thlA gene
source                  1..1179
                        mol_type = other DNA
                        organism = synthetic construct
SEQUENCE: 1
atgaaagaag ttgtaatagc tagtgcagta agaacagcga ttggatctta tggaaagtct  60
cttaaggatg taccagcagt agatttagga gctacagcta taaaggaagc agttaaaaaa 120
gcaggaataa aaccagagga tgttaatgaa gtcattttag gaaatgttct tcaagcaggt 180
ttaggacaga atccagcaag acaggcatct tttaaagcag gattaccagt tgaaattcca 240
gctatgacta ttaataaggt ttgtggttca ggacttagaa cagttagctt agcagcacaa 300
attataaaag caggagatgc tgacgtaata atagcaggtg gtatggaaaa tatgtctaga 360
gctccttact tagcgaataa cgctagatgg ggatatagaa tgggaaacgc taaatttgtt 420
gatgaaatga tcactgacgg attgtgggat gcatttaatg attaccacat gggaataaca 480
gcagaaaaca tagctgagag atggaacatt tcaagagaag aacaagatga gtttgctctt 540
gcatcacaaa aaaagctga agaagctata aaatcaggtc aatttaaaga tgaaatagtt 600
cctgtagtaa ttaaaggcag aaagggagaa actgtagttg atacagatga gcaccctaga 660
tttggatcaa ctatagaagg acttgcaaaa ttaaaacctg ccttcaaaaa agatggaaca 720
gttacagctg gtaatgcatc aggattaaat gactgtgcag cagtacttgt aatcatgagt 780
gcagaaaaag ctaaagagct tggagtaaaa ccacttgcta agatagtttc ttatggttca 840
gcaggagttg acccagcaat aatgggatat ggacctttct atgcaacaaa agcagctatt 900
gaaaaagcag gttggacagt tgatgaatta gatttaatag aatcaaatga agcttttgca 960
gctcaaagtt tagcagtagc aaaagattta aaatttgata tgaataaagt aaatgtaaat 1020
ggaggagcta ttgcccttgg tcatccaatt ggagcatcag gtgcaagaat actcgttact 1080
cttgtacacg caatgcaaaa aagagatgca aaaaaaggct tagcaacttt atgtataggt 1140
ggcggacaag gaacagcaat attgctagaa aagtgctag                       1179

SEQ ID NO: 2            moltype = DNA  length = 663
FEATURE                 Location/Qualifiers
misc_feature            1..663
                        note = polynucleotide sequence of atoD gene
source                  1..663
                        mol_type = other DNA
                        organism = synthetic construct
SEQUENCE: 2
```

```
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcacccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaaccccct gatagcccct   540
gcggctgata tcacgctggt agagccagat gaactggtcg aaaccggcga gctgcaacct   600
gaccatattg tcacccctgg tgccgttatc gaccacatca tcgtttcaca ggagagcaaa   660
taa                                                                 663

SEQ ID NO: 3          moltype = DNA  length = 651
FEATURE               Location/Qualifiers
misc_feature          1..651
                      note = polynucleotide sequence of atoA gene
source                1..651
                      mol_type = other DNA
                      organism = synthetic construct
SEQUENCE: 3
atggatgcga aacaacgtat tgcgcgccgt gtggcgcaag agcttcgtga tggtgacatc    60
gttaacttag ggatcggttt acccacaatg gtcgccaatt atttaccgga gggtattcat   120
atcactctgc aatcggaaaa cggcttcctc ggtttaggcc cggtcacgac agcgcatcca   180
gatctggtga acgctggcgg gcaaccgtgc ggtgttttac ccggtgcagc catgtttgat   240
agcgccatgt catttgcgct aatccgtggc ggtcatattg atgcctgcgt gctcggcggt   300
ttgcaagtag acgaagaagc aaacctcgcg aactggtag tgcctgggaa atggtgccc   360
ggtatgggtg gcgcgatgga tctggtgacc gggtcgcgca aagtgatcat cgccatggaa   420
cattgcgcca aagatggttc agcaaaaatt ttgcgccgct gcaccatgcc actcactgcg   480
caacatgcgg tgcatatgct ggttactgaa ctggctgtct ttcgttttat tgacggcaaa   540
atgtggctca ccgaaattgc cgacggtgt gatttagcca ccgtgcgtgc caaacagaa   600
gctcggtttg aagtcgccgc cgatctgaat acgaacggg gtgatttatg a             651

SEQ ID NO: 4          moltype = DNA  length = 735
FEATURE               Location/Qualifiers
misc_feature          1..735
                      note = polynucleotide sequence of adc gene
source                1..735
                      mol_type = other DNA
                      organism = synthetic construct
SEQUENCE: 4
atgttaaagg atgaagtaat taaacaaatt agcacgccat taacttcgcc tgcatttcct    60
agaggaccct ataaatttca taatcgtgag tattttaaca ttgtatatcg tacagatatg   120
gatgcacttc gtaaagttgt gccagagcct ttagaaattg atgagccctt agtcaggttt   180
gaaattatgg caatgcatga tacgagtgga cttggttgtt atacagaaag cggacaggct   240
attcccgtaa gctttaatgg agttaaggga gattatcttc atatgatgta tttagataat   300
gagcctgcaa ttgcagtagg aagggaatta agtgcatatc ctaaaaagct cgggtatcca   360
aagctttttg tggattcaga tactttagta ggaactttag actatggaaa acttagagtt   420
gcgacagcta caatggggta caaacataaa gcctagatg ctaatgaagc aaaggatcaa   480
atttgtcgcc ctaattatat gttgaaaata tacccaatt atgatggaag ccctagaata   540
tgtgagctta taaatgcgaa aatcacagat gttaccgtac atgaagcttg gacaggacca   600
actcgactgc agttatttga tcacgctatg gcgccactta atgatttgcc agtaaaagag   660
attgtttcta gctctcacat tcttgcagat ataatattgc ctagagctga agttatatat   720
gattatctta agtaa                                                    735

SEQ ID NO: 5          moltype = DNA  length = 1056
FEATURE               Location/Qualifiers
misc_feature          1..1056
                      note = polynucleotide sequence of sadh gene
source                1..1056
                      mol_type = other DNA
                      organism = synthetic construct
SEQUENCE: 5
atgaagggtt tcgcaatgct tggaattaac aagcttggat ggatcgagaa agagcggccc    60
gtggctggca gctatgatgc gattgtgcgc cccttgctg tgtctccttg tactagcgat   120
attcataccg tttttgaagg tgccctcggc gaccgtaaga acatgatcct cggccacgag   180
gctgttggag aagtggtcga agtaggttcg gaggtcaagg atttcaaacc aggtgaccgt   240
gtaatcgtcc cctgcaccac tccagattgg cgctcgttgg aggtgcaagc cggattccag   300
caacattcga atggtatgct cgccggttgg aagtttaaca atttcaaaga tggccgtattt   360
ggagaatact tccatgtaaa cgacgctgac atgaacctgg ctattctgcc taaagatatg   420
ccccttgaga acgcagtgat gatcacggat atgatgacga ctggttttca cggtgccgag   480
ctggcggata ttcagatggg atcctccgta gttgtcattg aattggcgc cgtgggcctt   540
atgggcattg ctggcgcaaa gcttcgggc gcggacgca ttattggcgt cggatcgcgt   600
cctatctgcg tagaggctgc gaaatttac gcgcaaaacc atcttgaa ctacaaaaac   660
ggccacatcg tagatcaagt gatgaagttg acgaatggca aagcgtcga tcgggtaatt   720
atggccggcg gaggcagcga gacccttcg caggctgtat caatggtcaa gcctggagga   780
atcatttcaa atatcaacta ccacggatca ggtgatgctc tgttgattcc acgtgtcgag   840
tggggatgcg gcatggccca aagacgatt aagggcggct gtgccctgg aggccgtctg   900
cgtgccgaaa tgctccgcga tatggtagtc tacaatcggg tggatctctc aaagctggtt   960
```

```
acccatgtct atcacggttt tgatcatatt gaggaggcgc tcctgctgat gaaggacaaa  1020
ccgaaggacc tcatcaaagc agtggttatc ctttaa                            1056

SEQ ID NO: 6              moltype = DNA   length = 1182
FEATURE                   Location/Qualifiers
misc_feature              1..1182
                          note = polynucleotide sequence of phaA gene
source                    1..1182
                          mol_type = other DNA
                          organism = synthetic construct
SEQUENCE: 6
atgactgacg ttgtcatcgt atccgccgcc cgcaccgcgg tcggcaagtt tggcggctcg   60
ctggccaaga tcccggcacc ggaactgggt gccgtggtca tcaaggccgc gctggagcgc  120
gccggcgtca agccggagca ggtgagcgaa gtcatcatgg gccaggtgct gaccgccggt  180
tcgggccaga accccgcacg ccaggccgcg atcaaggccg gctgccggc gatggtgccg   240
gccatgacca tcaacaaggt gtgcggctcg ggcctgaagg ccgtgatgct ggccgccaac  300
gcgatcatgg cgggcgacgc cgagatcgtg gtggccggcg ccaggaaaa catgagcgcc   360
gccccgcacg tgctgccggg ctcgcgcgat ggtttccgca tgggcgatgc caagctggct  420
gacaccatga tcgtcgacgg cctgtgggac gtgtacaacc agtaccacat gggcatcacc  480
gccgagaacg tggccaagga atacggcatc acacgcgagg cgcaggatga gttcgccgtc  540
ggctcgcaga acaaggccga agccgcgcag aaggccggca gtttgacga agagatcgtc   600
ccggtgctga tcccgcagcg caaggggcga ccggtgacca tcaagaccga cgagttcgtc   660
cgccagggcg ccacgctgga cagcatgtcc ggcctcaagc ccgccttcga caaggccggc   720
acggtgaccg cggccaacgc ctcgggcctg aacgacggcg ccgccgcggt ggtggtgatg   780
tcggcggcca aggccaagga actgggcctg accccgctgg ccacgatcaa gagctatgcc   840
aacgccggtc tcgatcccaa ggtgatgggc atgggcccgg tgccggcctc caagcgcgcc   900
ctgtcgcgcg ccgagtggac cccgcaagac ctggaccgta tggagatcaa cgaggccttt   960
gccgcgcagg cgctggcggt gcaccagcag atgggctggg acacctccaa ggtcaatgtg  1020
aacggcggcg ccatcgccat cggccacccg atcggcgcgt cgggctgccg tatcctggtg  1080
acgctgctgc acgagatgaa gcgccgtgac gcgaagaagg gcctggcctc gctgtgcatc  1140
ggcggcggca tgggcgtggc gctggcagtc gagcgcaaat aa                     1182

SEQ ID NO: 7              moltype = DNA   length = 702
FEATURE                   Location/Qualifiers
misc_feature              1..702
                          note = polynucleotide sequence of oxctA gene
source                    1..702
                          mol_type = other DNA
                          organism = synthetic construct
SEQUENCE: 7
atgaacaagg tctacgccag cgccgcagaa gcgcttgcag gcgtcgtccg cgacggccag   60
acgatcgccg tgggcggttt cggcctgtgc ggcatcccgc aggcgctgat tgccgcgctg  120
cgcgacagcg gcgccaagca gctgacctgt atctccaaca acgccggcgt cgatgcgttc  180
ggcctgggcc tgctgctggc cacgcgccag atcagcaaga tgatctcgtc ctacgtgggc  240
gagaacaagg agttcgagcg ccagtacctg cgggcgaac ttgagctgga attcaccccg   300
caaggcacgc tggccgagaa gctgcgcgcc ggcggctcgg catcccggc cttcttcacc   360
aagaccgtg tcggcaccat cgtcgccgaa ggcaaggaaa tccgcgaatt cgacggccag   420
cagtacgtga tggagcgttc gctgaccgcc gacgtggcgc tggtcaaggc atacaaggct   480
gacaaggccg gcaacctggt gttccgccgc accgcgcgca acttcaaccc gatgtgcgcc  540
atggcggca aggtcaccat cgccgaggtc gagcatatcg tcgagaccgg cgagctggac   600
ccggatgaaa tccaccctggc cggcatcttc gtgaagcgcc tggtgctgaa caccacccc   660
gagaaacgca tcgagcagcg caccgtgcgc gcggccagct aa                      702

SEQ ID NO: 8              moltype = DNA   length = 639
FEATURE                   Location/Qualifiers
misc_feature              1..639
                          note = polynucleotide sequence of oxctB gene
source                    1..639
                          mol_type = other DNA
                          organism = synthetic construct
SEQUENCE: 8
atggcatgga cacgtgacga aatggccgcg cgcgccgcga ccgagctgca ggacggtttc   60
tacgtcaacc tgggcatcgg cctgccgacg ctggtggcca actgggtgcc cgaaggcatg  120
gaagtgtggc tgcagtccga gaacggactg ctgggcatcg gccgttcc gaccgaggac    180
gaagtcgacg ccgacatgat caacgccggc aagcaaaccg tgacgacgct gccgggctcg  240
tcgatcttct cgtcggccga ctcgttcgcg atgatccgcg gcggccacat caacctggcg  300
atcctggtgt cgatgcaggt cagcgaaaag gcgacctggc caactggat gatcccgggc   360
aagatggtca agggcatggg cggcgcgatg gacctggtcg ccggcgtcgg ccgagtggtg  420
gtgctgatgg aacacaccgc caagaagaag gatggcaaca gggacatcaa gatcctgaag  480
gactgcaacc tgccgctgac cggcgtgggc gtggtcaacc gcatcattac cgacctgggc  540
gtgatcgacg tgaccgacga aggcctgaag ctggtggaaa cggctccggg tgtcagccgc  600
gaggaaatcc aggccaagac tggcgctccg ctgctgtaa                          639

SEQ ID NO: 9              moltype = DNA   length = 74
FEATURE                   Location/Qualifiers
misc_feature              1..74
                          note = polynucleotide sequence of L10 promoter
source                    1..74
                          mol_type = other DNA
```

```
                                 organism = synthetic construct
SEQUENCE: 9
gcagacggtt atggtcgccg ctaggtcttg gggagttttg ttcggtagtt atttattgtt    60
gaaggagata gatt                                                      74

SEQ ID NO: 10           moltype = DNA   length = 74
FEATURE                 Location/Qualifiers
misc_feature            1..74
                        note = polynucleotide sequence of I16 promoter
source                  1..74
                        mol_type = other DNA
                        organism = synthetic construct
SEQUENCE: 10
agacaccgcg tgcccgttat tctgtggggt gggtatagtt ctctagcgat gtggtgggct    60
acaggatatt attg                                                      74

SEQ ID NO: 11           moltype = DNA   length = 74
FEATURE                 Location/Qualifiers
misc_feature            1..74
                        note = polynucleotide sequence of H36 promoter
source                  1..74
                        mol_type = other DNA
                        organism = synthetic construct
SEQUENCE: 11
tctatctggt gccctaaacg ggggaatatt aacgggccca ggtggtcgc accttggttg     60
gtaggagtag catg                                                      74

SEQ ID NO: 12           moltype = DNA   length = 154
FEATURE                 Location/Qualifiers
misc_feature            1..154
                        note = polynucleotide sequence of Tac promoter
source                  1..154
                        mol_type = other DNA
                        organism = synthetic construct
SEQUENCE: 12
tcaaggcgca ctcccgttct ggataatgtt ttttgcgccg acatcataac ggttctggca    60
aatattctga aatgagctgt tgacaattaa tcatcggctc gtataatgtg tggaattgtg   120
agcggataac aatttcacac aggaaacaga atta                               154

SEQ ID NO: 13           moltype = DNA   length = 35
FEATURE                 Location/Qualifiers
misc_feature            1..35
                        note = primer_thlA_PstI_F
source                  1..35
                        mol_type = other DNA
                        organism = synthetic construct
SEQUENCE: 13
agactgcaga tgaaagaagt tgtaatagct agtgc                               35

SEQ ID NO: 14           moltype = DNA   length = 34
FEATURE                 Location/Qualifiers
misc_feature            1..34
                        note = primer_thlA_SalI_R
source                  1..34
                        mol_type = other DNA
                        organism = synthetic construct
SEQUENCE: 14
tgagtcgacc tagcactttt ctagcaatat tgct                                34

SEQ ID NO: 15           moltype = DNA   length = 46
FEATURE                 Location/Qualifiers
misc_feature            1..46
                        note = primer_atoD_SalI_F
source                  1..46
                        mol_type = other DNA
                        organism = synthetic construct
SEQUENCE: 15
atagtcgaca aggagatata catgaaaaca aaattgatga cattac                   46

SEQ ID NO: 16           moltype = DNA   length = 34
FEATURE                 Location/Qualifiers
misc_feature            1..34
                        note = primer_atoA_BamHI_R
source                  1..34
                        mol_type = other DNA
                        organism = synthetic construct
SEQUENCE: 16
ataggatcct cataaatcac cccgttgcgt attc                                34
```

```
SEQ ID NO: 17              moltype = DNA  length = 46
FEATURE                    Location/Qualifiers
misc_feature               1..46
                           note = primer_adc_BamHI_F
source                     1..46
                           mol_type = other DNA
                           organism = synthetic construct
SEQUENCE: 17
ataggatcca aggagatata catgttaaag gatgaagtaa ttaaac                    46

SEQ ID NO: 18              moltype = DNA  length = 39
FEATURE                    Location/Qualifiers
misc_feature               1..39
                           note = primer_adc_KpnI_R
source                     1..39
                           mol_type = other DNA
                           organism = synthetic construct
SEQUENCE: 18
tatggtacct tacttaagat aatcatatat aacttcagc                            39

SEQ ID NO: 19              moltype = DNA  length = 42
FEATURE                    Location/Qualifiers
misc_feature               1..42
                           note = primer_sAdh(opt)_KpnI_F
source                     1..42
                           mol_type = other DNA
                           organism = synthetic construct
SEQUENCE: 19
taggtaccaa ggagatatac atgaagggtt tcgcaatgct tg                        42

SEQ ID NO: 20              moltype = DNA  length = 37
FEATURE                    Location/Qualifiers
misc_feature               1..37
                           note = primer_sAdh(opt)_SacI_R
source                     1..37
                           mol_type = other DNA
                           organism = synthetic construct
SEQUENCE: 20
atagagctct taaaggataa ccactgcttt gatgagg                              37

SEQ ID NO: 21              moltype = DNA  length = 36
FEATURE                    Location/Qualifiers
misc_feature               1..36
                           note = primer_L10_GA_F
source                     1..36
                           mol_type = other DNA
                           organism = synthetic construct
SEQUENCE: 21
tgatttcatc aggaatgggc agacggttat ggtcgc                               36

SEQ ID NO: 22              moltype = DNA  length = 47
FEATURE                    Location/Qualifiers
misc_feature               1..47
                           note = primer_L10_GA_R
source                     1..47
                           mol_type = other DNA
                           organism = synthetic construct
SEQUENCE: 22
acaacttctt tcatggatcc aatctatctc cttcaacaat aaataac                   47

SEQ ID NO: 23              moltype = DNA  length = 38
FEATURE                    Location/Qualifiers
misc_feature               1..38
                           note = primer_I16_GA_F
source                     1..38
                           mol_type = other DNA
                           organism = synthetic construct
SEQUENCE: 23
tgatttcatc aggaatggag acaccgcgtg cccgttat                             38

SEQ ID NO: 24              moltype = DNA  length = 45
FEATURE                    Location/Qualifiers
misc_feature               1..45
                           note = primer_I16_GA_R
source                     1..45
                           mol_type = other DNA
                           organism = synthetic construct
SEQUENCE: 24
acaacttctt tcatggatcc caataatatc ctgtagccca ccaca                     45
```

| | | |
|---|---|---|
| SEQ ID NO: 25 | moltype = DNA length = 39 | |
| FEATURE | Location/Qualifiers | |
| misc_feature | 1..39 | |
| | note = primer_H36_GA_F | |
| source | 1..39 | |
| | mol_type = other DNA | |
| | organism = synthetic construct | |
| SEQUENCE: 25 | | |
| catcaggaat gggtcgactc tatctggtgc cctaaacgg | | 39 |
| | | |
| SEQ ID NO: 26 | moltype = DNA length = 29 | |
| FEATURE | Location/Qualifiers | |
| misc_feature | 1..29 | |
| | note = primer_H36_55_R | |
| source | 1..29 | |
| | mol_type = other DNA | |
| | organism = synthetic construct | |
| SEQUENCE: 26 | | |
| aatggatccc atgctactcc taccaacca | | 29 |
| | | |
| SEQ ID NO: 27 | moltype = DNA length = 35 | |
| FEATURE | Location/Qualifiers | |
| misc_feature | 1..35 | |
| | note = primer_PhaA_ClaI_F | |
| source | 1..35 | |
| | mol_type = other DNA | |
| | organism = synthetic construct | |
| SEQUENCE: 27 | | |
| tcatatcgat atgactgacg ttgtcatcgt atccg | | 35 |
| | | |
| SEQ ID NO: 28 | moltype = DNA length = 31 | |
| FEATURE | Location/Qualifiers | |
| misc_feature | 1..31 | |
| | note = primer_PhaA_BamHI_R | |
| source | 1..31 | |
| | mol_type = other DNA | |
| | organism = synthetic construct | |
| SEQUENCE: 28 | | |
| aatggatcct tatttgcgct cgactgccag c | | 31 |
| | | |
| SEQ ID NO: 29 | moltype = DNA length = 54 | |
| FEATURE | Location/Qualifiers | |
| misc_feature | 1..54 | |
| | note = primer_OxctA_GA_F | |
| source | 1..54 | |
| | mol_type = other DNA | |
| | organism = synthetic construct | |
| SEQUENCE: 29 | | |
| tcgagcgcaa ataaggatcc aaggagatat agatgaacaa ggtctacgcc agcg | | 54 |
| | | |
| SEQ ID NO: 30 | moltype = DNA length = 36 | |
| FEATURE | Location/Qualifiers | |
| misc_feature | 1..36 | |
| | note = primer_OxctA_GA_R | |
| source | 1..36 | |
| | mol_type = other DNA | |
| | organism = synthetic construct | |
| SEQUENCE: 30 | | |
| gccatctata tctcctttta gctggccgcg cgcacg | | 36 |
| | | |
| SEQ ID NO: 31 | moltype = DNA length = 37 | |
| FEATURE | Location/Qualifiers | |
| misc_feature | 1..37 | |
| | note = primer_OxctB_GA_F | |
| source | 1..37 | |
| | mol_type = other DNA | |
| | organism = synthetic construct | |
| SEQUENCE: 31 | | |
| gctaaaagga gatatagatg gcatggacac gtgacga | | 37 |
| | | |
| SEQ ID NO: 32 | moltype = DNA length = 39 | |
| FEATURE | Location/Qualifiers | |
| misc_feature | 1..39 | |
| | note = primer_OxctB_GA_R | |
| source | 1..39 | |
| | mol_type = other DNA | |
| | organism = synthetic construct | |
| SEQUENCE: 32 | | |

```
aaacaggcgg ccgcggtacc ttacagcagc ggagcgcca                              39

SEQ ID NO: 33          moltype = DNA  length = 41
FEATURE                Location/Qualifiers
misc_feature           1..41
                       note = primer_L10_POX_GA_F
source                 1..41
                       mol_type = other DNA
                       organism = synthetic construct
SEQUENCE: 33
aaaactttc gggatctcga ggcagacggt tatggtcgcc g                            41

SEQ ID NO: 34          moltype = DNA  length = 45
FEATURE                Location/Qualifiers
misc_feature           1..45
                       note = primer_L10_POX_GA_R
source                 1..45
                       mol_type = other DNA
                       organism = synthetic construct
SEQUENCE: 34
acaacgtcag tcatatcgat aatctatctc cttcaacaat aaata                       45

SEQ ID NO: 35          moltype = DNA  length = 41
FEATURE                Location/Qualifiers
misc_feature           1..41
                       note = primer_I16_POX_GA_F
source                 1..41
                       mol_type = other DNA
                       organism = synthetic construct
SEQUENCE: 35
aaaactttc gggatctcga gagacaccgc gtgcccgtta t                            41

SEQ ID NO: 36          moltype = DNA  length = 45
FEATURE                Location/Qualifiers
misc_feature           1..45
                       note = primer_I16_POX_GA_R
source                 1..45
                       mol_type = other DNA
                       organism = synthetic construct
SEQUENCE: 36
acaacgtcag tcatatcgat caataatatc ctgtagccca ccaca                       45

SEQ ID NO: 37          moltype = DNA  length = 45
FEATURE                Location/Qualifiers
misc_feature           1..45
                       note = primer_pMT_H36_GA_F
source                 1..45
                       mol_type = other DNA
                       organism = synthetic construct
SEQUENCE: 37
aaacttttcg ggatctcgag tctatctggt gccctaaacg gggga                       45

SEQ ID NO: 38          moltype = DNA  length = 49
FEATURE                Location/Qualifiers
misc_feature           1..49
                       note = primer_pMT_H36_GA_R
source                 1..49
                       mol_type = other DNA
                       organism = synthetic construct
SEQUENCE: 38
gatgacaacg tcagtcatgg atcccatgct actcctacca accaaggtg                   49
```

RECOMBINANT MICROORGANISM HAVING INCREASED ABILITY TO PRODUCE ISOPROPANOL AND METHOD OF PRODUCING ISOPROPANOL USING SAME

CROSS-REFERENCE TO RELATED APPLICATION

This application claims the benefit under 35 USC 119 (a) and 365 (b) of Korean Patent Application No. 10-2021-0185265, filed on Dec. 22, 2021 in the Korean Intellectual Property Office, the entire disclosure of which is incorporated herein by reference for all purposes.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The XML file submitted herewith contains a 56,680 bytes file (NewApp_0181810006_SequenceListing), which was created on Dec. 7, 2022.

BACKGROUND OF THE INVENTION

Field of the Invention

The present invention relates to an expression cassette for isopropanol production, a recombinant vector for isopropanol production including the expression cassette, a recombinant microorganism for isopropanol production into which the vector is introduced, and a method of producing isopropanol using the recombinant microorganism.

Description of the Related Art

Isopropanol is a structural isomer of 1-propanol and is propane in which one of hydrogens attached to central carbon is substituted with a hydroxyl group (—OH). Isopropanol serves as a protic solvent and is a secondary fatty acid and a secondary alcohol. Isopropanol is biosynthesized via a pathway using ATP and NADPH coenzymes starting from glucose.

Isopropanol is a colorless and flammable chemical having a strong odor as represented by the molecular formula $C_3H_8O$. Isopropanol mostly dissolves non-polar materials and evaporates quickly without leaving any residues, so it is widely used as a cleaning solution for IT parts such as semiconductors, LCDs, and the like, and is also used as a solvent for coatings such as paints, inks, and the like or for industrial processes.

The production of isopropanol through fermentation is possible in some *Clostridium* strains such as *Clostridium beijerinckii* NRRL B592, *C. beijerinckii* NRRL B593, *C. beijerinckii* IAM 19015, *C. beijerinckii* ATCC 14823, *C. beijerinckii* NCIMB 9581, and the like. However, the concentration of isopropanol that is produced by the above strains is very low, which is undesirable.

Meanwhile, the production strain *Corynebacterium glutamicum* is a Gram-positive strain and is considered to be appropriate for isopropanol production as a strain suitable for high-density growth restriction. However, there is a problem in that isopropanol is produced in a small amount in the existing *Corynebacterium glutamicum* and glucose is not mainly used.

Against this background, the present inventors have made great efforts to develop technology capable of increasing the amount of isopropanol that is produced, and thus ascertained when that, using a recombinant microorganism in which a succinic acid bypass metabolic pathway is introduced to the isopropanol production pathway, the ability to produce isopropanol may be increased, thereby culminating in the present invention.

SUMMARY OF THE INVENTION

Accordingly, it is an object of the present invention to provide a first expression cassette for isopropanol production.

It is another object of the present invention to provide a second expression cassette for isopropanol production.

It is still another object of the present invention to provide a recombinant vector for isopropanol production including the first expression cassette.

It is yet another object of the present invention to provide a recombinant vector for isopropanol production including the second expression cassette.

It is still yet another object of the present invention to provide a recombinant microorganism for isopropanol production into which the two vectors are introduced.

It is even yet another object of the present invention to provide a method of producing isopropanol using the recombinant microorganism.

In order to accomplish the above objects, the present invention provides a first expression cassette for isopropanol production including a thlA gene represented by the nucleotide sequence of SEQ ID NO: 1, an atoD gene represented by the nucleotide sequence of SEQ ID NO: 2, an atoA gene represented by the nucleotide sequence of SEQ ID NO: 3, an adc gene represented by the nucleotide sequence of SEQ ID NO: 4, and a sadh gene represented by the nucleotide sequence of SEQ ID NO: 5.

In addition, the present invention provides a second expression cassette for isopropanol production including a phaA gene represented by the nucleotide sequence of SEQ ID NO: 6, an oxctA gene represented by the nucleotide sequence of SEQ ID NO: 7, and an oxctB gene represented by the nucleotide sequence of SEQ ID NO: 8.

In an embodiment of the present invention, the first expression cassette may further include a promoter for enhancing gene expression.

In an embodiment of the present invention, the promoter may be selected from the group consisting of an L10 promoter represented by the nucleotide sequence of SEQ ID NO: 9, an I16 promoter represented by the nucleotide sequence of SEQ ID NO: 10, and a H36 promoter represented by the nucleotide sequence of SEQ ID NO: 11.

In an embodiment of the present invention, the second expression cassette may further include a Tac promoter.

In an embodiment of the present invention, the Tac promoter may have the nucleotide sequence represented by SEQ ID NO: 12.

In addition, the present invention provides a recombinant vector for isopropanol production including the first expression cassette.

In addition, the present invention provides a recombinant vector for isopropanol production including the second expression cassette.

In addition, the present invention provides a recombinant microorganism for isopropanol production into which the two vectors are introduced.

In addition, the present invention provides a method of producing isopropanol including culturing the recombinant microorganism.

In an embodiment of the present invention, the microorganism may be *Corynebacterium glutamicum*.

In an embodiment of the present invention, the recombinant microorganism may be cultured in a medium containing sodium citrate.

BRIEF DESCRIPTION OF THE DRAWINGS

The above and other objects, features, and other advantages of the present invention will be more clearly understood from the following detailed description taken in conjunction with the accompanying drawings, in which:

FIGS. 2A to 2C show results confirming cell growth and metabolite production of a recombinant *Corynebacterium* strain with an isopropanol metabolic pathway gene introduced thereto (FIG. 2A: cell growth rate and consumed glucose, FIG. 2B: produced acetone, and FIG. 2C: produced isopropanol);

FIGS. 3A to 3F show results confirming cell growth and metabolite production of the recombinant *Corynebacterium* strain with the isopropanol metabolic pathway gene and a synthetic promoter for enhancing gene expression introduced thereto (FIG. 3A: cell growth rate and consumed glucose, FIG. 3B: produced acetone, FIG. 3C: produced isopropanol, FIG. 3D: produced lactic acid, FIG. 3E: produced acetic acid, and FIG. 3F: produced succinic acid);

DETAILED DESCRIPTION OF THE INVENTION

Figure 1A:
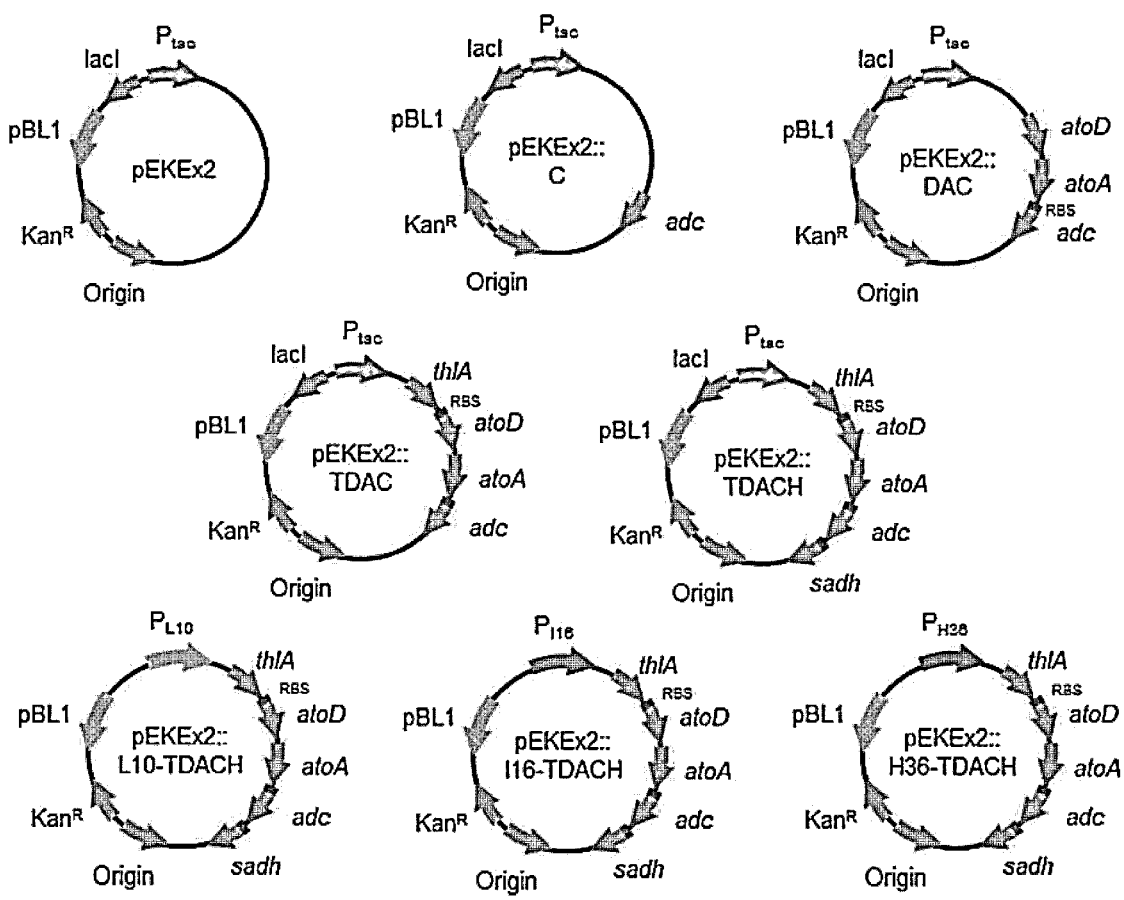
FIGS. 1A and 1B show a vector map of recombinant vectors constructed in the present invention.

Hereinafter, a detailed description will be given of the present invention.

An aspect of the present invention pertains to a first expression cassette for isopropanol production including a thlA gene represented by the nucleotide sequence of SEQ ID NO: 1, an atoD gene represented by the nucleotide sequence of SEQ ID NO: 2, an atoA gene represented by the nucleotide sequence of SEQ ID NO: 3, an adc gene represented by the nucleotide sequence of SEQ ID NO: 4, and a sadh gene represented by the nucleotide sequence of SEQ ID NO: 5, and a vector for isopropanol production including the same.

In the present invention, the thlA gene is a gene encoding acetyl-CoA acetyltransferase, and the thlA gene of the present invention may be derived from a *Clostridium acetobutylicum* strain and may be represented by the nucleotide sequence of SEQ ID NO: 1.

In the present invention, the atoD gene is a gene encoding an acetate CoA-transferase subunit alpha, and the atoD gene of the present invention may be derived from *Escherichia coli* and may be represented by the nucleotide sequence of SEQ ID NO: 2.

In the present invention, the atoA gene is a gene encoding an acetate CoA-transferase subunit beta (atoA), and the atoA gene of the present invention may be derived represented by the nucleotide sequence of SEQ ID NO: 3.

In the present invention, the adc gene is a gene from *Escherichia* encoding acetoacetate decarboxylase, and the adc gene of the present invention may be derived from a *Clostridium acetobutylicum* strain and may be represented by the nucleotide sequence of SEQ ID NO: 4.

In the present invention, the sadh gene is a gene encoding isopropanol dehydrogenase (secondary alcohol dehydrogenase), and the sadh gene of the present invention may be derived from a *Clostridium beijerinckii* strain, and may be subjected to codon optimization so that it is well expressed in *Corynebacterium glutamicum*. The codon-optimized sadh gene may be represented by the nucleotide sequence of SEQ ID NO: 5.

Another aspect of the present invention pertains to a second expression cassette for isopropanol production including a phaA gene represented by the nucleotide sequence of SEQ ID NO: 6, an oxctA gene represented by the nucleotide sequence of SEQ ID NO: 7, and an oxctB gene represented by the nucleotide sequence of SEQ ID NO: 8, and a vector for isopropanol production including the same.

In the present invention, the phaA gene is a gene encoding beta-ketothiolase, and the phaA gene of the present invention may be derived from a *Ralstonia eutropha* or *Cupriavidus necator* strain and may be represented by the nucleotide sequence of SEQ ID NO: 6.

In the present invention, the oxctA gene is a gene encoding acetoacetate CoA-transferase, and the oxctA gene of the present invention may be derived from a *Ralstonia eutropha* or *Cupriavidus necator* strain and may be represented by the nucleotide sequence of SEQ ID NO: 7.

In the present invention, the oxctB gene is a gene encoding a pyruvate dehydrogenase E1 component, and the oxctB gene of the present invention may be derived from a *Ralstonia eutropha* or *Cupriavidus necator* strain and may be represented by the nucleotide sequence of SEQ ID NO: 8.

The first expression cassette of the present invention preferably further includes a promoter for enhancing gene expression.

Examples of the promoter for enhancing gene expression may include an L10 promoter represented by the nucleotide sequence of SEQ ID NO: 9, an I16 promoter represented by the nucleotide sequence of SEQ ID NO: 10, and a H36 promoter represented by the nucleotide sequence of SEQ ID NO: 11, but are not particularly limited thereto.

The second expression cassette of the present invention may further include a Tac promoter, and the Tac promoter may have the nucleotide sequence represented by SEQ ID NO: 12.

In the present invention, the expression cassette indicates a unit cassette that includes a promoter and a gene encoding a target protein and is capable of being expressed to produce a target protein operably linked downstream of the promoter. Various factors that may assist in efficient production of the target protein may be included inside or outside the expression cassette. Specifically, the target protein expression cassette may be configured such that a gene encoding the target protein is operably linked downstream of the promoter sequence.

Also, variants of the gene are within the scope of the present invention. Specifically, the eight genes (thlA, atoD, atoA, adc, sadh, phaA, oxctA, and oxctB) have a sequence homology of 70% or more, preferably 80% or more, more preferably 90% or more, most preferably 95% or more with the nucleotide sequence of the sequence number corresponding to each gene, and include a sequence that exhibits substantially the same physiological activity. The "% sequence homology" with a polynucleotide is identified by comparing two optimally arranged sequences with a comparison region, and a portion of the polynucleotide sequence in the comparison region may include additions or deletions (i.e. gaps) compared to a reference sequence (not including additions or deletions) for the optimal arrangement of the two sequences.

As used herein, the term "operably linked" means that the gene sequence and the promoter sequence are functionally linked so that the nucleic acid sequence having promoter activity of the present invention initiates and mediates transcription of a gene encoding a target protein. The operable linkage may be prepared using recombinant DNA technology known in the art, and site-specific DNA cleavage and ligation may be made using cleavage and ligation enzymes in the art, but the present invention is not limited thereto. Specifically, the expression cassette of the present invention may be inserted into the chromosome of a host cell to produce a recombinant microorganism, and it is obvious to those skilled in the art to which the present invention belongs that, even when the expression cassette is inserted into the genomic chromosome of the host cell, the same effect as when the recombinant vector is introduced into the host cell may be exhibited. A method of inserting the expression cassette into the chromosome of the host cell may include a typically known gene manipulation method, for example, a method using a retroviral vector, an adenoviral vector, an adeno-associated viral vector, a herpes simplex virus vector, a poxvirus vector, a lentiviral vector, or a non-viral vector.

In the present invention, the vector is a DNA construct containing a DNA sequence that is operably linked to a suitable control sequence capable of expressing DNA in a suitable host. The vector may be a plasmid, a phage particle, or simply a potential genomic insert. Upon transformation into an appropriate host, the vector may replicate and function independently of the host genome, or in some cases may be integrated into the genome itself. Since a plasmid is currently the most common form of the vector, "plasmid" and "vector" are sometimes used interchangeably herein. However, the present invention includes other forms of vectors that serve equivalent functions and are or will be known in the art.

In the present invention, the recombinant vector may be used as an expression vector for a target polypeptide capable of expressing the target polypeptide with high efficiency in an appropriate host cell when the gene encoding the target polypeptide to be expressed is operably linked. The recombinant vector may be expressed in a host cell. The host cell is preferably a eukaryotic cell, and an expression control sequence such as a promoter, terminator, enhancer, etc., a sequence for membrane targeting or secretion, and the like may be appropriately selected depending on the type of host cell and may be combined in various ways depending on the purpose.

Still another aspect of the present invention pertains to a recombinant microorganism for isopropanol production into which the two recombinant vectors (a recombinant vector for isopropanol production including the first expression cassette and a recombinant vector for isopropanol production including the second expression cassette) are introduced.

In the present invention, the recombinant microorganism is transformed with the two recombinant vectors of the present invention (a recombinant vector for isopropanol production including the first expression cassette and a recombinant vector for isopropanol production including the second expression cassette). As used herein, the term "transformation" means introducing the vector including the promoter according to the present invention or additionally the gene encoding a target protein into a host cell. Moreover, so long as the gene encoding the transformed target protein may be expressed in the host cell, it may be inserted into the chromosome of the host cell or located extrachromosomally.

In the present invention, the two recombinant vectors (a recombinant vector for isopropanol production including the first expression cassette and a recombinant vector for isopropanol production including the second expression cassette) may be introduced into the microorganism sequentially or in a reverse order.

Yet another aspect of the present invention pertains to a method of producing isopropanol including culturing the recombinant microorganism described above.

The recombinant microorganism for isopropanol production according to the present invention may be a strain of the genus *Corynebacterium* (*Clostridium*), preferably *Corynebacterium glutamicum*.

In the method of producing isopropanol according to the present invention, the recombinant microorganism is preferably cultured in a medium containing sodium citrate.

A better understanding of the present invention may be obtained through the following examples. These examples are merely set forth to illustrate the present invention and are not to be construed as limiting the scope of the present invention.

EXAMPLES

Materials

*Clostridium acetobutylicum* ATCC 824 was obtained from Dr. Eum Youngsoon's research team (KIST), *Ralstonia eutropha* H16 or *Cupriavidus necator* H16 (KCTC 1006) was purchased from Korean Collection for Type Cultures (KCTC), a pMT-tac vector was produced in the laboratory (Korean Patent No. 10-1756338), a pEKEx2 vector was obtained from Professor Wu research Hanmin's team (Sungkyunkwan University), and Bacto Brain Heart Infusion (BHI) medium was purchased from BD (Becton, Dickinson and Company, di-237500). For reference, *Ralstonia eutropha* H16 and *Cupriavidus necator* H16 are the same strain.

Example 1

Obtaining thlA, atoD, atoA, adc, sadh, phaA, oxctA, oxctB Gene Resources

In a *Corynebacterium glutamicum* strain, genes related to an isopropanol metabolic pathway were heterologously expressed and overexpressed. From genomic DNA (gDNA) of *Clostridium acetobutylicum* ATCC 824, the gene thlA encoding acetyl-CoA acetyltransferase and the gene adc encoding acetoacetate decarboxylase were obtained. From gDNA of *Escherichia coli*, the gene atoD encoding the acetate CoA-transferase subunit alpha and the gene atoA encoding the acetate CoA-transferase subunit beta were obtained. The gene sadh encoding isopropanol dehydrogenase derived from *Clostridium beijerinckii* NRRL B593 was subjected to codon optimization so as to be well expressed in *Corynebacterium glutamicum*.

For genes involved in enhancing the succinic acid metabolic pathway, the gene phaA encoding beta-ketothiolase, the gene OxctA encoding acetoacetate CoA-transferase, and the gene OxctB encoding the pyruvate dehydrogenase E1 component were obtained from gDNA of a strain known as *Ralstonia eutropha* H16 or *Cupriavidus necator* H16.

Expression of each gene was regulated by lacI and individual forward and reverse primers including the corresponding restriction enzyme sequence of the vector were synthesized for cloning into a pMT-tac or pEKEx2 vector having tac a promoter for high expression. Polymerase chain reaction (PCR) was performed using the synthesized primers. Primer information of individual gene resources is shown in Table 1 below, and forward and reverse primers are represented in the order of the genes described above.

Consequently, the thlA gene of 1179 bp, the atoD gene of 663 bp, the atoA gene of 651 bp, the adc gene of 735 bp, the synthesized sadh gene of 1056 bp, the phaA gene of 1182 bp, the OxctA gene of 702 bp, and the OxctB gene of 639 bp were obtained. The nucleotide sequences of individual genes were represented in SEQ ID NOs: 1 to 8. Also, in the present invention, synthetic promoters L10, I16, and H36 were used to enhance the expression of the introduced gene, and the nucleotide sequences of these genes were represented in SEQ ID NOs: 9 to 11.

| Primer sequences used for gene amplification | |
|---|---|
| Primer | SEQ ID No. |
| thlA PstI F | 13 |
| thlA SalI R | 14 |
| atoD SalI F | 15 |
| atoA BamHI R | 16 |
| adc BamHI F | 17 |
| adc KpnI R | 18 |
| sAdh(opt) KpnI F | 19 |
| sAdh(opt) SacI R | 20 |
| L10 GA F | 21 |
| L10 GA R | 22 |
| I16 GA F | 23 |
| I16 GA R | 24 |
| H36 GA F | 25 |
| H36 55 R | 26 |
| PhaA ClaI F | 27 |
| PhaA BamHI R | 28 |
| OxctA GA F | 29 |
| OxctA GA R | 30 |
| OxctB GA F | 31 |
| OxctB GA R | 32 |
| L10 POX GA F | 33 |
| L10 POX GA R | 34 |
| I16 POX GA F | 35 |
| I16 POX GA R | 36 |
| pMT H36 GA F | 37 |
| pMT H36 GA R | 38 |

Example 2

Figure 1B:
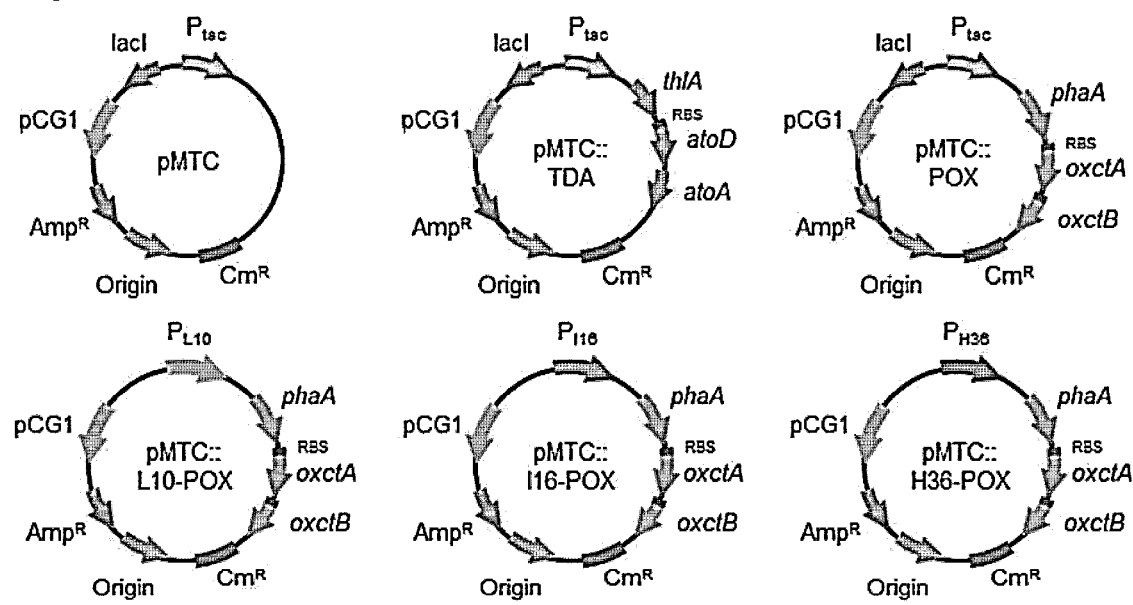

Construction of Recombinant Vector and Recombinant Microorganism Containing thlA, atoD, atoA, adc, sadh, phaA, oxctA, oxctB Gene Resources Thus Obtained In order to construct a recombinant vector, pMTC and pEKEx2 vectors were used as *E. coli-C. glutamicum* shuttle vectors, and 'AAGGAGATATAG' for the pMTC vector or 'AAGGAGATATAC' for the pEKEx2 vector was used as a ribosome-binding site (RBS) and inserted upstream of the gene. As such, the thlA, atoA, and phaA genes did not require RBS insertion because the promoter was present upstream thereof or was bound with the gene. For T4 DNA ligation, insert DNA and vector DNA were each digested with an appropriate restriction enzyme (New England Biolab) and then ligated with T4 DNA ligase (Enzynomics) in the form of a mixture. For Gibson assembly, the insert DNA was treated with DpnI as required, and the vector DNA was digested with an appropriate restriction enzyme and then ligated with the Gibson assembly kit (New England Biolab) in the form of a mixture. All experiments for constructing recombinant vectors were performed according to the manufacturer's instructions. All recombinant vectors constructed in the present invention are summarized in detail in Table 2 below, and each vector map is shown in FIGS. 1A and 1B. Transformation of the recombinant vector into *E. coli* was performed through a heat shock method at 42° C.

The transformation method for heterologous expression of the recombinant vector synthesized in *E. coli* with a *Corynebacterium glutamicum* strain was performed in the following manner. Specifically, the *Corynebacterium* strain in a competent state stored at a cryogenic temperature (−80° C.) was slowly thawed for 15 minutes. Thereafter, the target gene was injected into 80 µl of competent cells. The cells were allowed to stand on ice for 20 minutes and then transferred to a pre-chilled 0.2 cm cuvette (Bio-Rad, USA) for electroporation. Electroporation was performed at a voltage of 2.5 kV and a resistance value of 200 Ω. Thereafter, 1 ml of BHI (brain-heart infusion) medium (BHISG) containing sorbitol and glucose was immediately placed in the cuvette containing the cells, followed by heat shock treatment at 46° C. for 6 minutes. After recovery at 30° C. for 2-3 hours, the cells were seeded in a BHISG agar plate containing kanamycin (25 mg/L) and spectinomycin (100 mg/L), followed by culture at 30° C. for 2-3 days.

In order to confirm transformation of the recombinant microorganism, colony PCR was performed as follows. After obtaining one colony, construction of the recombinant vector was confirmed by targeting the pBL1 origin site for pEKEx2 vector confirmation and the pCG1 site for the pMTC vector confirmation. Transformation of *Corynebacterium glutamicum* was performed in the same manner as above. All recombinant microorganisms constructed in the present invention are shown in detail in Table 3 below.

TABLE 2

Recombinant vectors constructed in the present invention

| Vector | Characteristics |
|---|---|
| pEKEx2 | $P_{tac}$, lacI, $Kan^R$, pBL1 ori; *C. glutamicum-E. coli* shuttle vector for regulating gene expression |
| pEKEx2 C | pEKEx2 carrying adc gene from *Clostridium acetobutylicum* ATCC 824 |
| pEKEx2 DAC | pEKEx2 carrying atoD, atoA genes from *E. Coli* and adc gene |
| pEKEx2 TDAC | pEKEx2 carrying thlA gene from *Clostridium acetobutylicum* ATCC 824 and atoD, atoA, adc genes |
| pEKEx2 TDACH | pEKEx2 carrying thlA, atoD, atoA, adc genes and sadh gene from *Clostridium beijerinckii* codon optimized for *C. glutamicum* |
| pEKEx2 L10-TDACH | pEKEx2 carrying thlA, atoDA, adc, sadh genes with promoter change to $P_{L10}$ |
| pEKEx2 I16-TDACH | pEKEx2 carrying thlA, atoDA, adc, sadh genes with promoter change to $P_{I16}$ |
| pEKEx2 H36-TDACH | pEKEx2 carrying thlA, atoDA, adc, sadh genes with promoter change to $P_{H36}$ |
| pMTC | $P_{tac}$, lacI, $Amp^R$, $Cm^R$, pCG1 ori : *C. glutamicum-E. coli* shuttle vector |

TABLE 2-continued

Recombinant vectors constructed in the present invention

| Vector | Characteristics |
|---|---|
| pMTC TDA | pMTC carrying thlA, atoD, atoA genes |
| pMTC POX | pMTC carrying phaA, OxctA, OxctB genes from Ralstonia eutropha |
| pMTC L10-POX | pMTC carrying phaA, OxctA, OxctB genes with promoter change to $P_{L10}$ |
| pMTC I16-POX | pMTC carrying phaA, OxctA, OxctB genes with promoter change to $P_{I16}$ |
| pMTC H36-POX | pMTC carrying phaA, OxctA, OxctB genes with promoter change to $P_{H36}$ |

TABLE 3

Mutant microorganisms of the present invention

| Strain | Characteristics |
|---|---|
| Escherichia coli DH5α | F−, deoR, endA1, gyrA96, hsdR17(rk−mk+), recA1, relA1, supE44, thi-1, Δ(lacZYA-argF) U169, (Phi80/acZdeIM15) |
| C. glutamicum ATCC 13032 | Wild-type |
| TDA/H36-TDACH | C. glutamicum ATCC 13032 derivative; [pMTC TDA with pEKEx2 H36-TDACH] |
| POX/H36-TDACH | C. glutamicum ATCC 13032 derivative; [pMTC POX with pEKEx2 H36-TDACH] |
| L10-POX/H36-TDACH | C. glutamicum ATCC 13032 derivative; [pMTC L10-POX with pEKEx2 H36-TDACH] |
| I16-POX/H36-TDACH | C. glutamicum ATCC 13032 derivative; [pMTC I16-POX with pEKEx2 H36-TDACH] |
| H36-POX/H36-TDACH | C. glutamicum ATCC 13032 derivative; [pMTC_H36-POX with pEKEx2 H36-TDACH] |

Example 3

Confirmation of Isopropanol Production Using Recombinant Microorganism

For culture of E. coli for gene cloning, LB medium containing 5 g/L yeast extract, 10 g/L tryptone, and 10 g/L NaCl was used. Pre-culture of the Corynebacterium strain was carried out in a nutrient medium containing 37 g/L BHI medium, 91 g/L sorbitol, and 20 g/L glucose. Main culture for target product production was carried out in a mixed medium containing 15 g/L ammonium chloride ($NH_4Cl$), 10 g/L ammonium sulfate (($NH_4$)$_2SO_4$), 10 g/L sodium citrate ($Na_3C_6H_5O_7$), 40 g/L glucose, 10 g/L yeast extract, 1 g/L urea, 0.5 g/L potassium dihydrogen phosphate ($KH_2PO_4$), 0.5 g/L dipotassium hydrogen phosphate ($K_2HPO_4$), 1 g/L $MgSO_4 \cdot 7H_2O$, 200 μg/L biotin, and 100 μg/L thiamine. The medium was supplemented with kanamycin (25 mg/L), ampicillin (50 mg/L for E. coli), and chloramphenicol (33 mg/L for E. coli, 10 mg/L for Corynebacterium glutamicum), as necessary. 1 mM isopropyl β-D-1-thiogalactopyranoside (IPTG), and 1× trace element (10 g/L iron (II) sulfate heptahydrate, 10 g/L manganese (II) sulfate, 1 g/L zinc sulfate heptahydrate, 0.31 g/L copper (II) sulfate pentahydrate, and 0.02 g/L nickel (II) chloride hexahydrate) were added at the beginning of flask culture, followed by batch culture. In order to find a component that plays a major role in the production of isopropanol in the mixed medium, culture was carried out in a mixed medium excluding ammonium chloride and a mixed medium excluding sodium citrate.

The flask culture process was performed as follows. All wild-type and recombinant Corynebacterium strains stored at cryogenic temperatures were streaked on BHISG agar plates, followed by culture at 30° C. for 24 hours. Thereafter, one colony was inoculated into 20 mL of BHISG medium, followed by pre-culture at 30° C. and 200 rpm for 16 hours. The pre-cultured cells were seeded in a 250 mL baffled flask containing 50 mL of CGAF medium at an optical density (OD) of 600 nm adjusted to a concentration of 1. Main culture was carried out with shaking at 30° C. and 200 rpm for 48 hours.

Cell growth was measured at an optical density of 600 nm using a UV-vis spectrophotometer (Mecasys Co., Ltd.). The pretreatment process for the measurement of intracellular isopropanol, glucose, and various organic acids was as follows. In order to isolate the cells, 1 mL of the culture fluid was centrifuged at 13,000 rpm for 2 minutes. The supernatant obtained after cell extraction was quantitatively analyzed using a high-performance liquid chromatography (HPLC) system (Waters Corporation).

The results thereof are shown in detail in FIGS. 2A to 2C, 3A to 3F, 4A to 4F, and 5A and 5B.

Figure 2A:
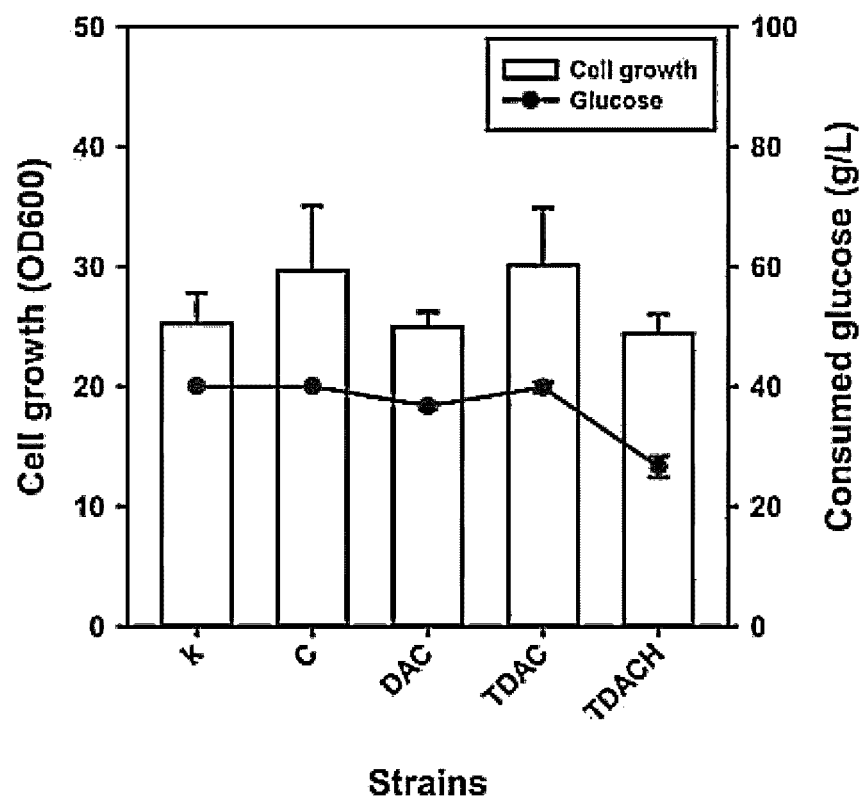
Figure 2C:
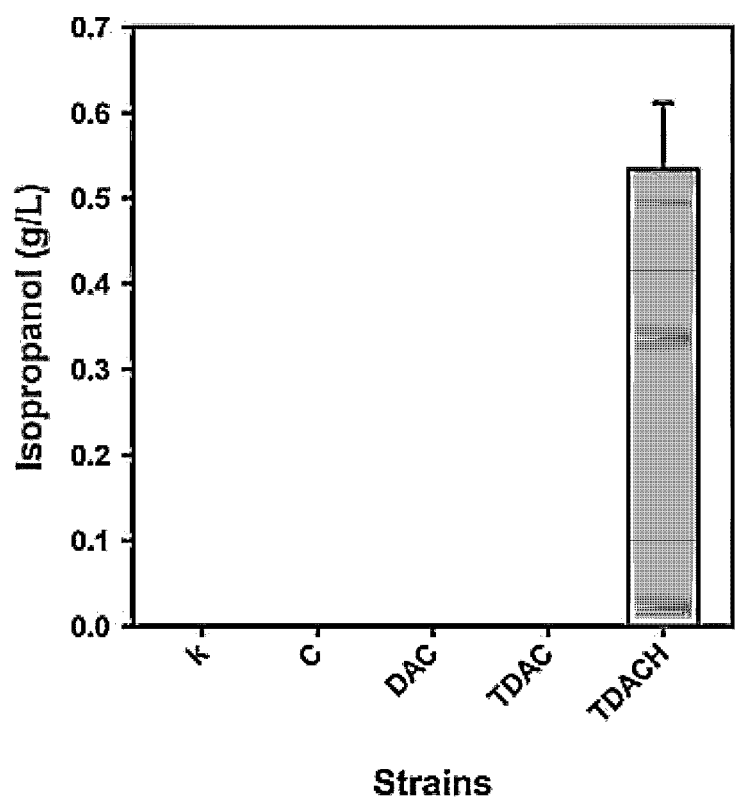

First, based on results confirming cell growth and metabolite production of the recombinant Corynebacterium strain into which the isopropanol metabolic pathway gene was introduced, acetone was produced in the Corynebacterium strain into which the pEKEx2_TDAC vector was introduced (FIG. 2B), and 0.53 g/L of isopropanol was produced only in the Corynebacterium strain into which the pEKEx2_TDACH vector was introduced (FIG. 2C).

Figure 3A:
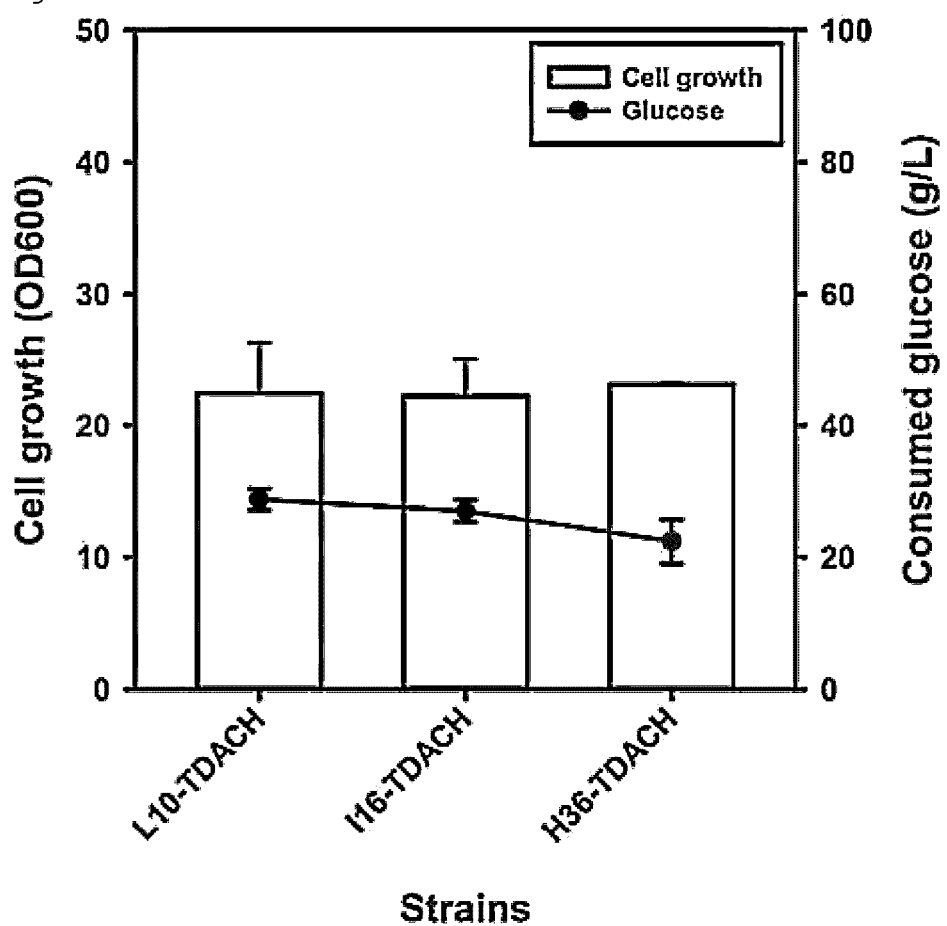
Figure 3C:
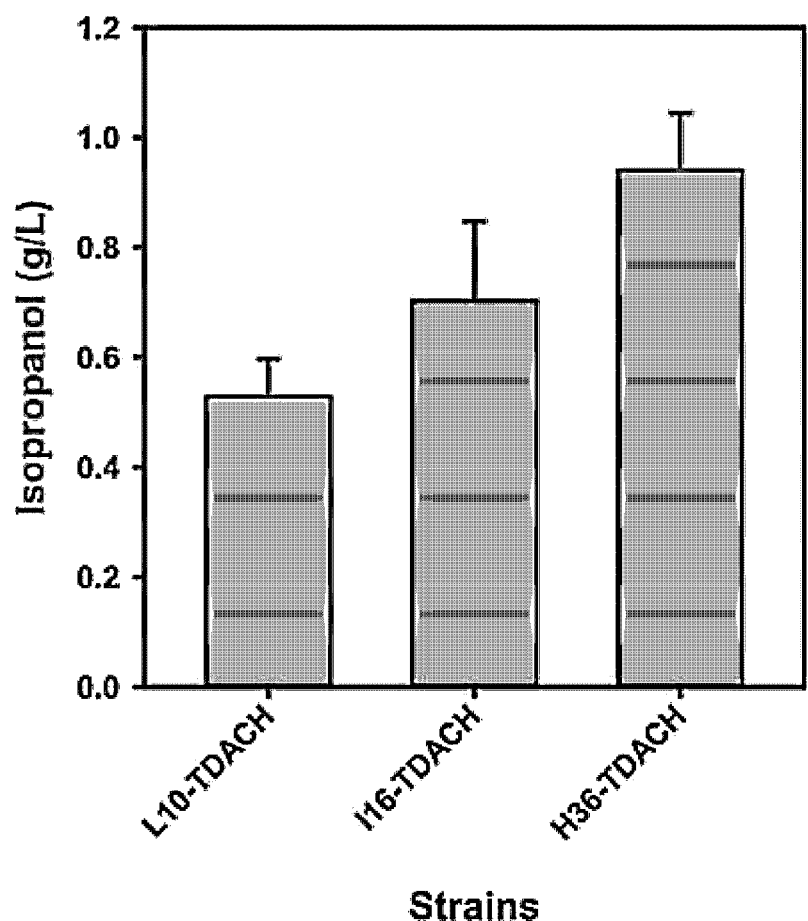
Figure 3D:
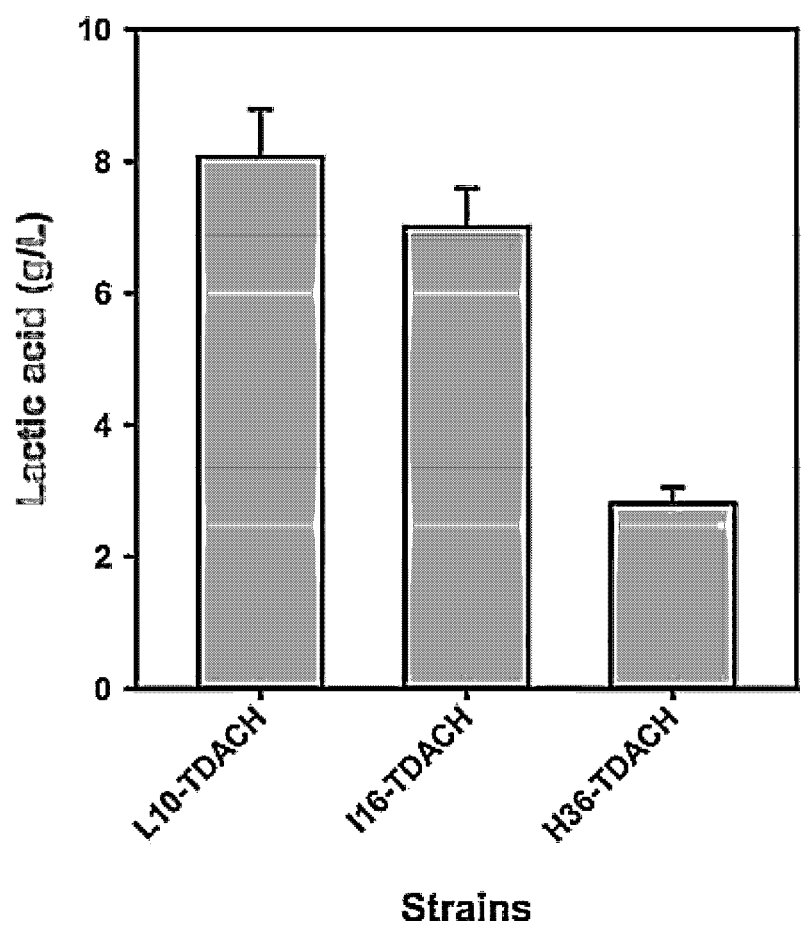
Figure 3E:
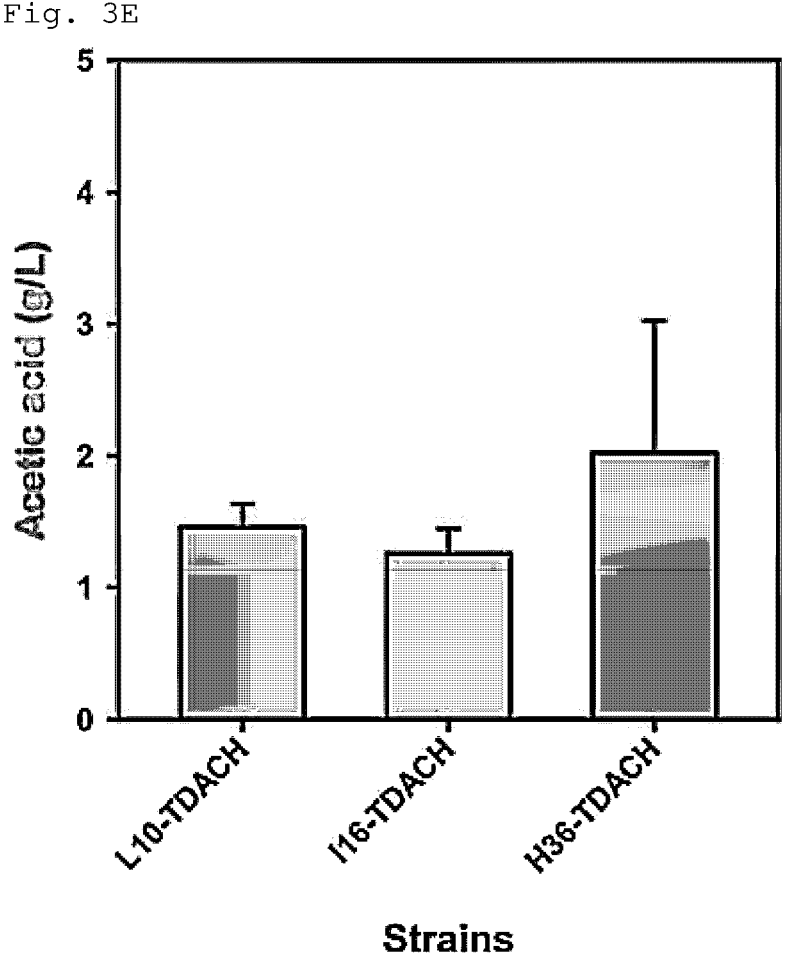
Figure 3F:
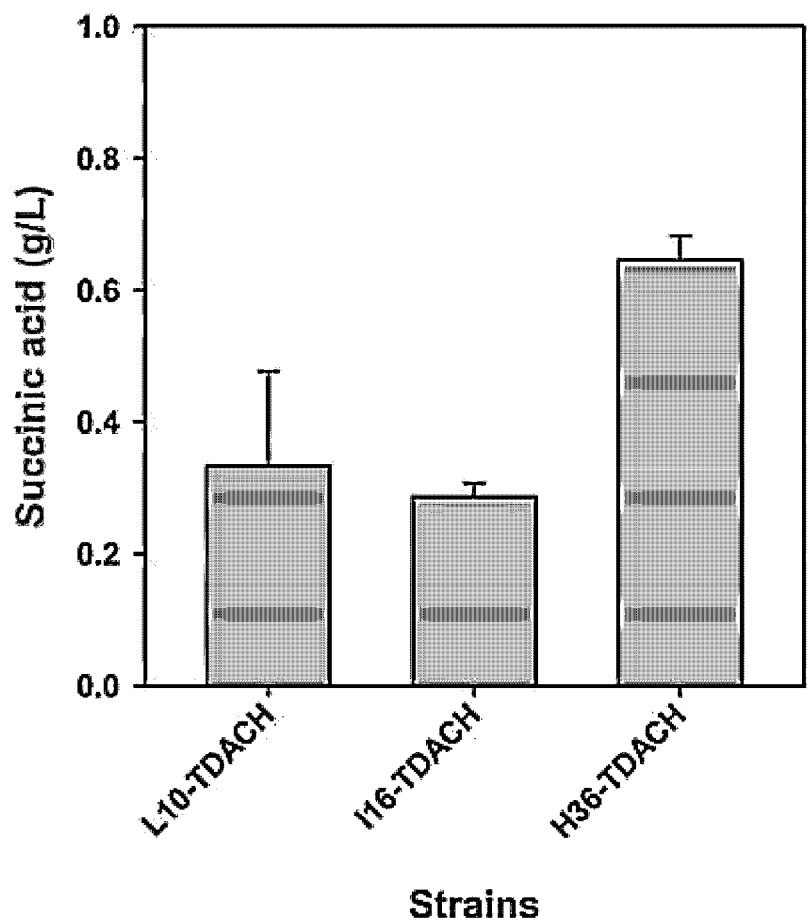

Also, based on results confirming cell growth and metabolite production of the recombinant Corynebacterium strain into which both the isopropanol metabolic pathway gene and a synthetic promoter for enhancing gene expression were introduced together, the production of isopropanol was generally increased in the strain with the synthetic promoter (L10, I16, or H36) introduced thereinto compared to the strain using the conventional tac promoter (FIG. 3C). Specifically, 0.53 g/L of isopropanol was produced in the Corynebacterium strain into which the PEKEx2_L10-TDACH vector was introduced, 0.7 g/L of isopropanol was produced in the Corynebacterium strain into which the pEKEx2_I16-TDACH vector was introduced, and 0.94 g/L of isopropanol was produced in the Corynebacterium strain into which the pEKEx2_H36-TDACH vector was introduced. These values are 1.8 times higher than when using the conventional tac promoter. In addition to isopropanol, lactic acid (FIG. 3D), acetic acid (FIG. 3E), and succinic acid (FIG. 3F) were produced as incidental metabolites, and succinic acid was produced in a large amount in the Corynebacterium strain into which the pEKEx2_H36-TDACH vector was introduced, compared to other recombinant strains.

Figure 4A:
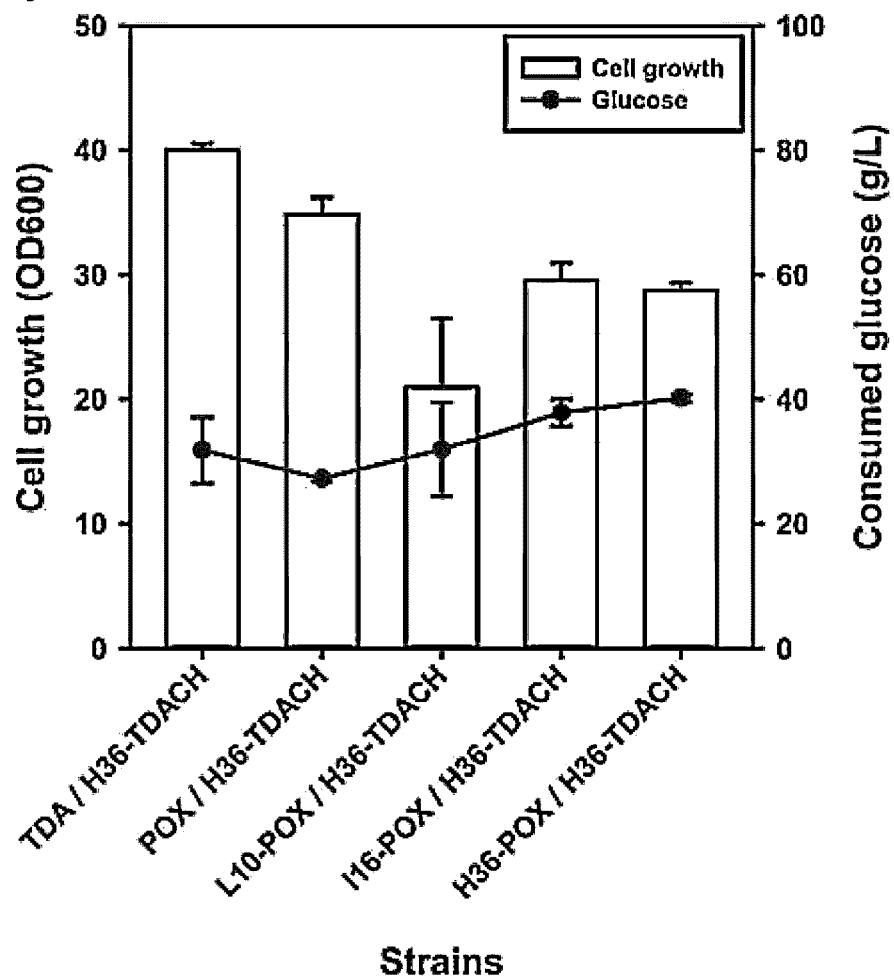
FIGS. 4A to 4F show results confirming cell growth and metabolite production of the recombinant *Corynebacterium* strain with the isopropanol metabolic pathway gene and a succinic acid bypass pathway gene introduced thereinto (FIG. 4A: cell growth rate and consumed glucose, FIG. 4B: produced acetone, FIG. 4C: produced isopropanol, FIG. 4D: produced lactic acid, FIG. 4E: produced acetic acid, and FIG. 4F: produced succinic acid)
Figure 4B:
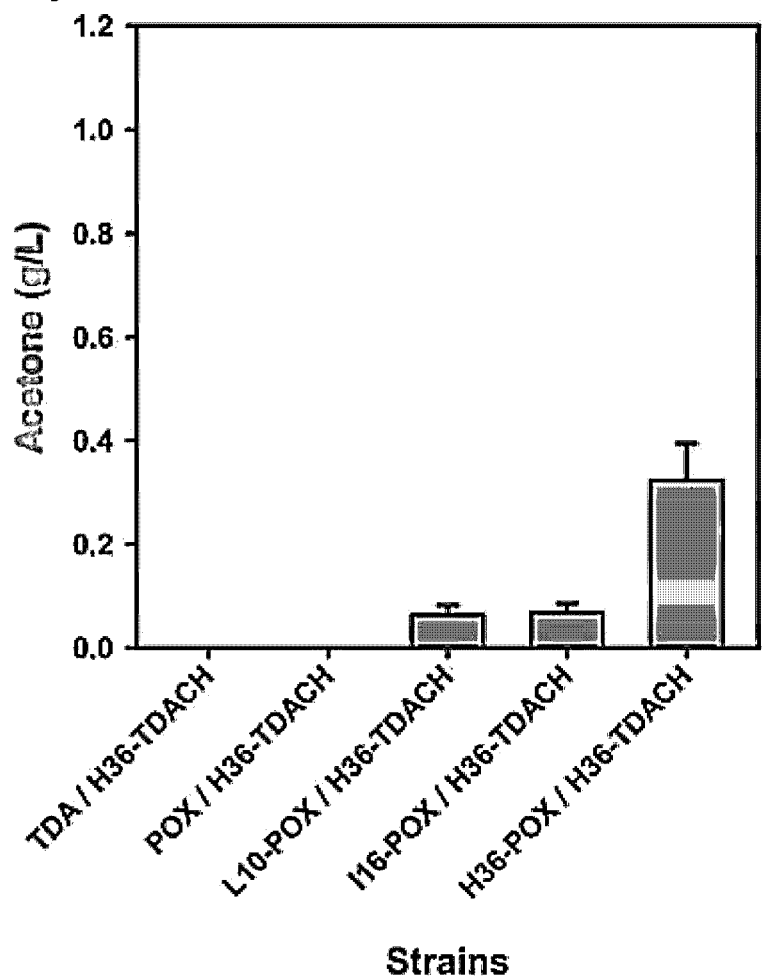
Figure 4C:
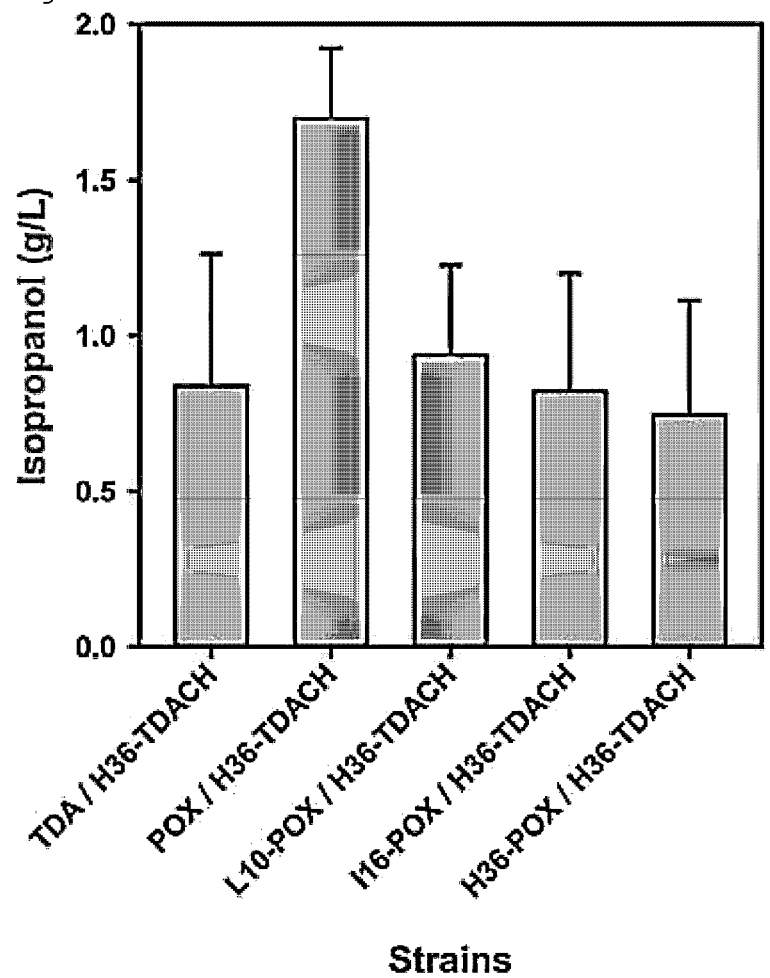
Figure 4D:
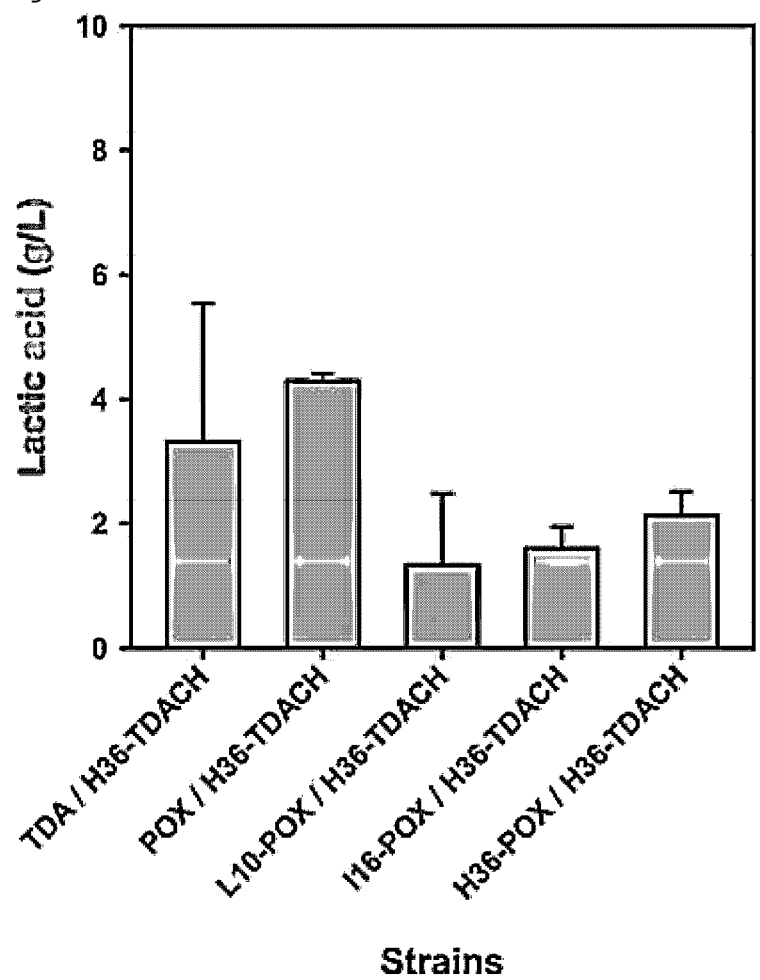
Figure 4E:
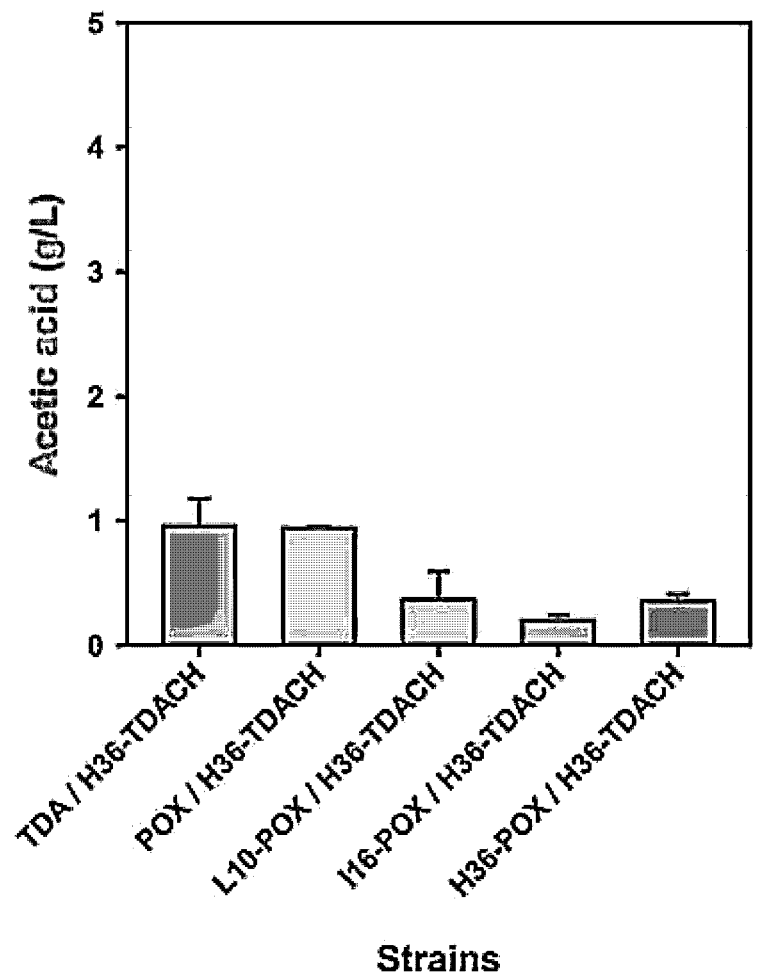
Figure 4F:
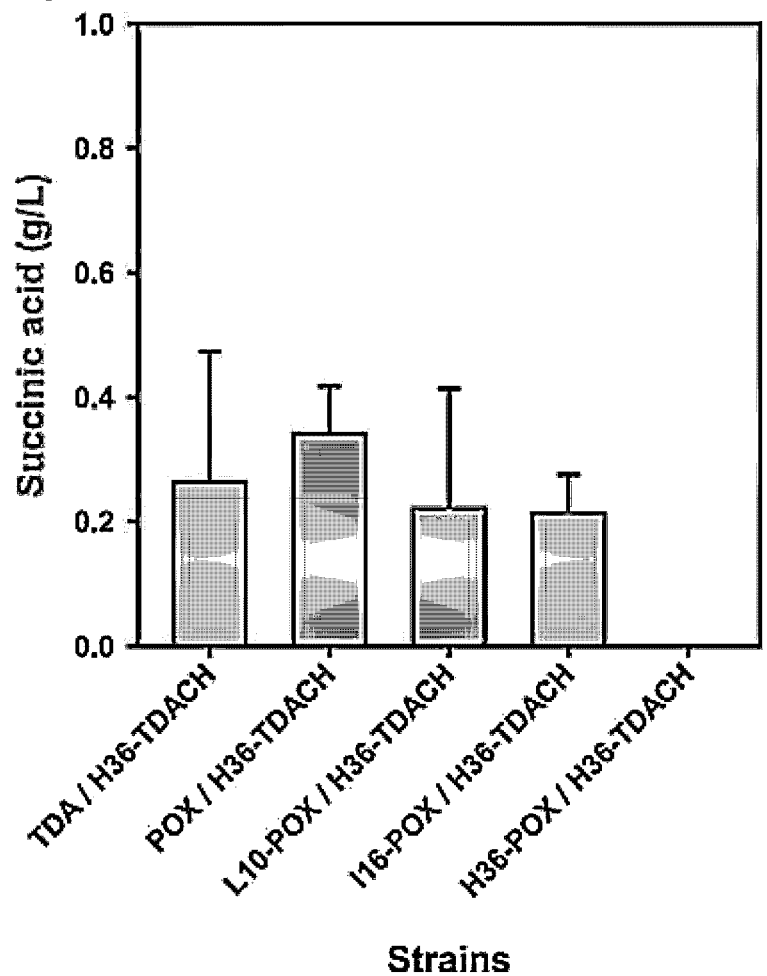

Also, based on results confirming cell growth and metabolite production of the recombinant Corynebacterium strain into which both the isopropanol metabolic pathway gene and a succinic acid bypass pathway gene were introduced together, 1.7 g/L of isopropanol was produced in the Corynebacterium strain into which the two vectors pEKEx2_H36-TDACH and pMTC_POX were introduced, indicating that isopropanol production was increased 2.24 times compared to the Corynebacterium strain (0.76 g/L) into which the pEKEx2_H36-TDACH vector was introduced as the control (FIG. 4C). Such a recombinant strain was confirmed to have not only the increased ability to produce isopropanol but also the ability to produce acetone (FIG. 4B). However, in the Corynebacterium strains with the two vectors pEKEx2_H36-TDACH and pMTC_L10-POX (or pMTC_I16-POX, pMTC_H36-POX) introduced thereinto, isopropanol was produced in respective amounts of 0.94, 0.82, and 0.74 g/L, and thus there was no actual increase in effect due to introduction of these two vectors compared to the *Corynebacterium* strain into which the pEKEx2_H36-TDACH vector was introduced alone. Based on such results, it was confirmed that the *Corynebacterium* strain into which the two vectors pEKEx2_H36-TDACH and pMTC_POX were introduced was optimized for isopropanol production. In addition to isopropanol, lactic acid (FIG. 4D), acetic acid (FIG. 4E), and succinic acid (FIG. 4F) were produced as incidental metabolites, and the production of succinic acid was reduced compared to the *Corynebacterium* strain with the pEKEx2_H36-TDACH vector alone introduced thereinto. Based on the above results, it was confirmed that the isopropanol production was increased by the use of the succinic acid pathway in the *Corynebacterium* strain into which the two vectors pEKEx2_H36-TDACH and pMTC_POX were introduced, compared to the *Corynebacterium* strain into which the pEKEx2_H36-TDACH vector was introduced alone.

Also, the results of FIGS. 2A, 3A, 4A, and 5A show cell growth and consumed glucose, indicating that the growth of cells does not affect inhibition of isopropanol production, which means that glucose was consumed well to thus produce isopropanol.

Moreover, cell growth and metabolite production were confirmed in a major-component-defined mixed medium for *Corynebacterium* for isopropanol production. For reference, the *Corynebacterium* strain used in this experiment is a strain into which the pEKEx2_TDACH vector is introduced.

Figure 5A:
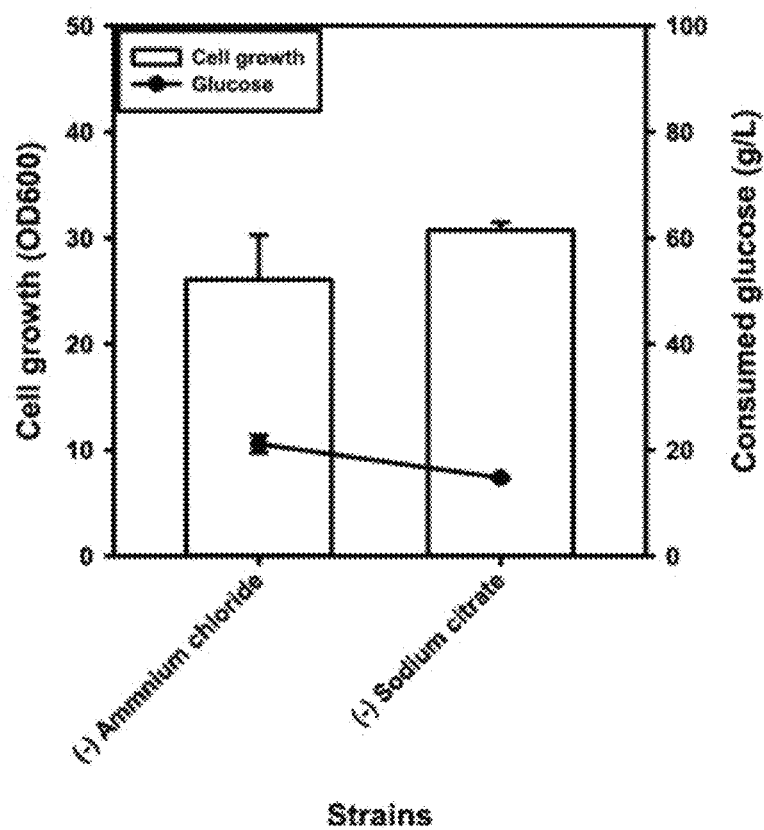
FIGS. 5A and 5B show results confirming cell growth and metabolite production in a major-component-defined mixed medium for the recombinant *Corynebacterium* strain for isopropanol production according to the present invention (FIG. 5A: cell growth rate and consumed glucose and FIG. 5B: produced isopropanol).
Figure 5B:
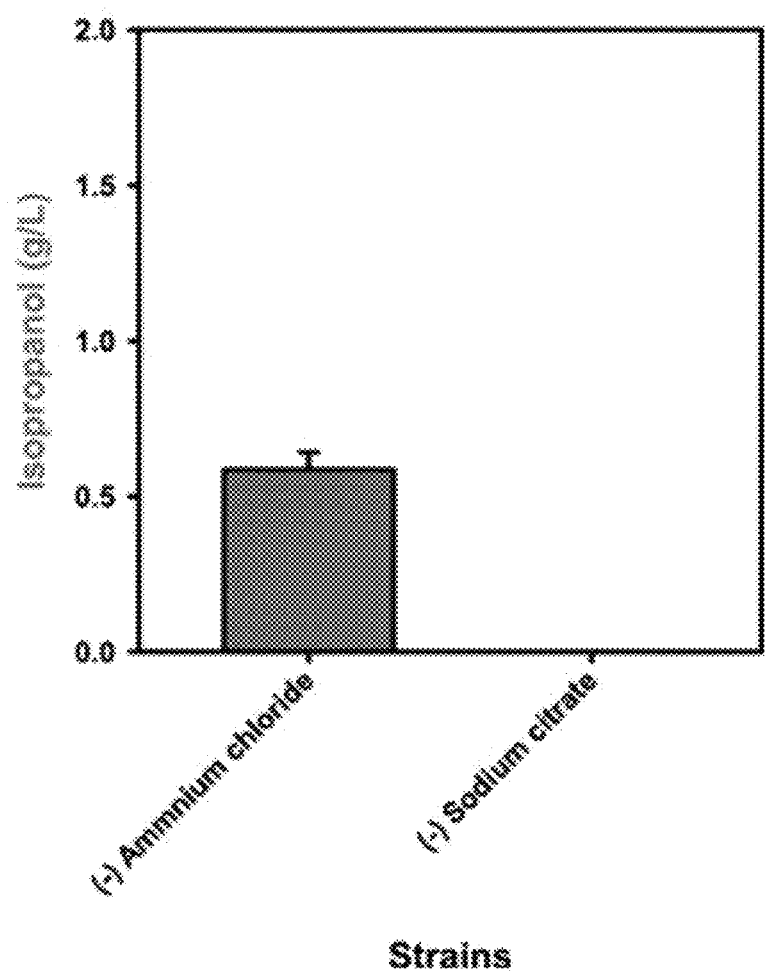

Consequently, as shown in FIGS. 5A and 5B, isopropanol was not produced in the absence of sodium citrate, confirming that sodium citrate is an essential component for isopropanol production.

As is apparent from the above description, according to the present invention, a recombinant microorganism for isopropanol production in which a succinic acid bypass metabolic pathway is introduced to an isopropanol production pathway has greatly increased ability to produce isopropanol. In particular, the recombinant microorganism for isopropanol production according to the present invention is capable of producing isopropanol in an amount corresponding to about 100 times the maximum amount of isopropanol that is produced using the existing *Corynebacterium glutamicum*. Therefore, the recombinant microorganism for isopropanol production according to the present invention can effectively produce isopropanol and can be useful in various industrial fields where isopropanol is utilized. In addition, the use of the recombinant microorganism of the present invention makes it possible to produce high-value-added isopropanol materials for manufacturing biomass-derived chemical products using glucose in lieu of petroleum in an eco-friendly manner.

Although preferable exemplary embodiments of the present invention have been disclosed in detail above, it will be obvious to those skilled in the art that the present invention may be implemented in a modified form without departing from the essential characteristics of the present invention. Therefore, the disclosed embodiments are to be considered in an illustrative rather than a restrictive way. The scope of the present invention is indicated in the claims rather than the foregoing description, and all differences within the scope equivalent thereto should be construed as being included in the present invention.

What is claimed is:

1. A first expression cassette for isopropanol production, comprising:
   a thlA gene consisting of SEQ ID NO: 1;
   an atoD gene consisting of SEQ ID NO: 2;
   an atoA gene consisting of SEQ ID NO: 3;
   an adc gene consisting of SEQ ID NO: 4; and
   a sadh gene consisting of SEQ ID NO: 5.

2. The first expression cassette according to claim 1, further comprising a promoter for enhancing gene expression.

3. The first expression cassette according to claim 2, wherein the promoter is selected from the group consisting of: an L10 promoter consisting of SEQ ID NO: 9, an I16 promoter consisting of SEQ ID NO: 10, and a H36 promoter consisting of SEQ ID NO: 11.

4. A recombinant vector for isopropanol production, comprising the first expression cassette according to claim 1.

5. A recombinant microorganism for isopropanol production into which a first recombinant vector for isopropanol production comprising a first expression cassette and a second recombinant vector for isopropanol production comprising a second expression cassette are introduced,
   wherein the first expression cassette comprises:
   a thlA gene consisting of SEQ ID NO: 1;
   an atoD gene consisting of SEQ ID NO: 2;
   an atoA gene consisting of SEQ ID NO: 3;

an adc gene consisting of SEQ ID NO: 4; and
a sadh gene consisting of SEQ ID NO: 5, and
wherein the second expression cassette comprises:
a phaA gene consisting of SEQ ID NO: 6;
an oxctA gene consisting of SEQ ID NO: 7; and
an oxctB gene consisting of SEQ ID NO: 8.

6. A method of producing isopropanol, comprising culturing the recombinant microorganism according to claim 5, wherein the recombinant microorganism is cultured in a medium containing sodium citrate.

7. The method according to claim 6, wherein the microorganism is *Corynebacterium glutamicum*.

* * * * *